United States Patent
Ghosh et al.

(10) Patent No.: US 9,474,457 B2
(45) Date of Patent: *Oct. 25, 2016

(54) METRICS OF ELECTRICAL DYSSYNCHRONY AND ELECTRICAL ACTIVATION PATTERNS FROM SURFACE ECG ELECTRODES

(71) Applicant: Medtronic, Inc., Minneapolis, MN (US)

(72) Inventors: Subham Ghosh, Blaine, MN (US); Jeffrey M Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/190,578

(22) Filed: Feb. 26, 2014

(65) Prior Publication Data

US 2014/0371808 A1 Dec. 18, 2014

Related U.S. Application Data

(60) Provisional application No. 61/834,133, filed on Jun. 12, 2013.

(51) Int. Cl.
*A61N 1/37* (2006.01)
*A61B 5/0408* (2006.01)
(Continued)

(52) U.S. Cl.
CPC ......... *A61B 5/04085* (2013.01); *A61B 5/0452* (2013.01); *A61B 5/6805* (2013.01); *A61B 5/7282* (2013.01); *A61N 1/3627* (2013.01); *A61N 1/3682* (2013.01); *A61N 1/3684* (2013.01)

(58) Field of Classification Search
CPC ............................ A61N 1/371; A61N 1/3684
USPC ............................................................ 607/28
See application file for complete search history.

(56) References Cited

U.S. PATENT DOCUMENTS

| 4,233,987 A | 11/1980 | Feingold |
| 4,428,378 A | 1/1984 | Anderson et al. |

(Continued)

FOREIGN PATENT DOCUMENTS

| CN | 1043621 A | 7/1990 |
| EP | 1 072 284 A2 | 1/2001 |

(Continued)

OTHER PUBLICATIONS

Biffi et al., "Occurrence of Phrenic Nerve Stimulation in Cardiac Resynchronization Therapy Patients: the Role of Left Ventricular Lead Type and Placement Site," *Europace*, 2013; 15:77-82.

(Continued)

*Primary Examiner* — Alyssa M Alter
(74) *Attorney, Agent, or Firm* — Carol F. Barry

(57) ABSTRACT

A method and system of cardiac pacing is disclosed. A baseline rhythm is determined using a plurality of body-surface electrodes. A set of baseline functional electrical metrics is determined in response to determining the baseline rhythm. Resynchronization pacing is delivered using a right ventricular electrode and a pacing left ventricular electrode or only with a left ventricular electrode. A set of functional electrical metrics relating to cardiac depolarization and repolarization is determined in response to resynchronization pacing. A determination is made as to whether relative reduction of at least one functional electrical metric from the set of functional electrical metrics exceeds X % of its corresponding value from the set of baseline functional electrical metrics. A determination is made as to whether an absolute value of at least one electrical metric from the set of the functional electrical metrics is less than Y ms. A determination is made as to whether a site is responsive to cardiac resynchronization therapy (CRT).

47 Claims, 15 Drawing Sheets

(51) Int. Cl.
*A61B 5/00* (2006.01)
*A61B 5/0452* (2006.01)
*A61N 1/362* (2006.01)
*A61N 1/368* (2006.01)

(56) References Cited

U.S. PATENT DOCUMENTS

| | | |
|---|---|---|
| 4,497,326 A | 2/1985 | Curry |
| 4,566,456 A | 1/1986 | Koning et al. |
| 4,674,511 A | 6/1987 | Cartmell |
| 4,763,660 A | 8/1988 | Kroll et al. |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,443,492 A | 8/1995 | Stokes et al. |
| 5,514,163 A | 5/1996 | Markowitz et al. |
| 5,628,778 A | 5/1997 | Kruse et al. |
| 5,671,752 A | 9/1997 | Sinderby et al. |
| 5,683,432 A | 11/1997 | Goedeke et al. |
| 5,810,740 A | 9/1998 | Paisner |
| 5,891,045 A | 4/1999 | Albrecht et al. |
| 5,922,014 A | 7/1999 | Warman et al. |
| 6,055,448 A | 4/2000 | Anderson et al. |
| 6,187,032 B1 | 2/2001 | Ohyu et al. |
| 6,236,883 B1 | 5/2001 | Ciaccio et al. |
| 6,311,089 B1 | 10/2001 | Mann et al. |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,473,638 B2 | 10/2002 | Ferek-Petric |
| 6,480,745 B2 | 11/2002 | Nelson et al. |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,640,136 B1 | 10/2003 | Helland et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |
| 8,617,082 B2 | 12/2013 | Zhang et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,805,504 B2 | 8/2014 | Sweeney |
| 8,972,228 B2 | 3/2015 | Ghosh et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 2002/0161307 A1 | 10/2002 | Yu et al. |
| 2003/0018277 A1 | 1/2003 | He |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0122479 A1 | 6/2004 | Spinelli et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |

(56) References Cited

U.S. PATENT DOCUMENTS

| | | |
|---|---|---|
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Gosh et al. |
| 2012/0284003 A1 | 11/2012 | Gosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |

FOREIGN PATENT DOCUMENTS

| | | |
|---|---|---|
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 98/26712 A1 | 6/1998 |
| WO | WO 00/45700 A1 | 8/2000 |
| WO | WO 01/67950 A1 | 9/2001 |
| WO | 03/070323 A1 | 8/2003 |
| WO | WO 2005/056108 A2 | 6/2005 |
| WO | 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | 2007/027940 A2 | 3/2007 |
| WO | WO 2007/013994 A3 | 4/2007 |
| WO | 2007/027940 A3 | 6/2007 |
| WO | WO 2007/139456 A1 | 12/2007 |
| WO | WO 2008/151077 A2 | 12/2008 |
| WO | 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |

(56) References Cited

FOREIGN PATENT DOCUMENTS

| WO | WO 2011/070166 A1 | 6/2011 |
|---|---|---|
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

"CardioGuide System Enables Real-Time Navigation of Left Ventricular Leads During Medtronic CRT Implants," Press Release, Apr. 9, 2013, Medtronic, Inc., 2 pgs.

Cuculich, P.S., et al., "The Electrophysiological Cardiac Ventricular Substrate in Patients After Myocardial Infection" *J. Am. Coll. Cardiol.* 2011; 58:1893-1902.

Czerwinska et al., "Method of Segmentation of Thorax Organs Images Applied to Modeling the Cardiac Electrical Field," *Engineering in Medicine and Biology Society*, Proceedings of the 22nd Annual International Conference of the IEEE, vol. 1, 23, Jul. 23, 2000.; pp. 402-405.

Dawoud, F. et al., "Inverse Electrocardiographic Imaging to Assess Electrical Dyssynchrony in Cardiac Resynchronization Therapy Patients," *Computing in Cardiology*, 2012; 39:993-996.

Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.

Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.

Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.

Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.

Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.

Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.

Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.

Hayes et al., "Cardiac Resynchronization Therapy and the Relationship of Percent Biventricular Pacing to Symptoms and Survival," *Heart Rhythm*, Sep. 2011; 8(9):1469-1475.

"Heart Failure Management" datasheet [online]. Medtronic, Minneapolis, Minnesota, [Last updated on Jun. 3, 2013].Retrieved from the Internet: www.medtronic.com; 9 pages.

Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.

Kornreich, "Body Surface Potential Mapping of ST Segment Changes in Acute Myocardial Infarction," *Circulation*, 1993; 87: 773-782.

Medtronic Vitatron CARELINK ENCORE® Programmer Model 29901 Reference Manual, 2013, Medtronic, Inc., Minneapolis, MN.

Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.

Potse et al., "Mathematical Modeling and Simulation of Ventricular Activation Sequences: Implications for Cardiac Resynchronization Therapy," *J. of Cardiovasc. Trans. Res.*, 2012; 5:146-158.

Prinzen et al., "Cardiac Resynchronization Therapy State-of-the-Art of Current Applications, Guidelines, Ongoing Trials, and Areas of Controversy" Circulation, 2013; 128: 2407-2418.

Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.

Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.

Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.

Steinhaus BM., "Estimating cardiac transmembrane activation and recovery times from unipolar and bipolar extracellular electrograms : a simulation study," *Circulation Research*, 1989, 64:449-462.

Strik et al., "Electrical and Mechanical Ventricular Activation During Left Bundle Branch Block and Resynchronization," *J. of Cardiovasc. Trans. Res.*, 2012; 5:117-126.

Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-634.

Turner et al, "Electrical and Mechanical Components of Dyssynchrony in Heart Failure Patients with Normal QRS Duration and Left Bundle-Branch Block," *Circulation* 2004; 109: 2544-2549.

Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

Miri et al., "Applicability of body surface potential map in computerized optimization of biventricular pacing," *Annals of Biomedical Engineering*, vol. 38, No. 3, Mar. 2010, pp. 865-875.

(56) References Cited

OTHER PUBLICATIONS

Miri et al., "Comparison of the electrophysiologically based optimization methods with different pacing parameters in patient undergoing resynchronization treatment," *30th Annual International IEEE EMBS Conference,* Aug. 2008, pp. 1741-1744.

Miri et al., "Computerized Optimization of Biventricular Pacing Using Body Surface Potential Map," *31st Annual International Conference of the IEEE EMBS,* Sep. 2009, pp. 2815-2818.

Miri et al., "Efficiency of Timing Delays and Electrode Positions in Optimization of Biventricular Pacing: A Simulation Study," *IEEE Transactions on Biomedical Engineering,* Nov. 2009, pp. 2573-2582.

Svendsen et al., "Computational Models of Cardiac Electrical Activation," Chapter 5, Computational Nov. 2010, pp. 73-88.

Wang et al., "Application of the Method of Fundamental Solutions to Potential-based Inverse Electrocardiography," *Annals of Biomedical Engineering,* Aug. 2006, pp. 1272-1288.

METRICS OF ELECTRICAL DYSSYNCHRONY AND ELECTRICAL ACTIVATION PATTERNS FROM SURFACE ECG ELECTRODES

CROSS-REFERENCE TO RELATED APPLICATIONS

This application claims the benefit of U.S. Provisional Application No. 61/834,133, filed on Jun. 12, 2013. The disclosure of the above application is incorporated herein by reference in its entirety.

TECHNICAL FIELD

The disclosure relates to electrophysiology and, more particularly, to evaluating the electrical activation patterns of the heart.

BACKGROUND

The beat of the heart is controlled by the sinoatrial node, a group of conductive cells located in the right atrium near the entrance of the superior vena cava. The depolarization signal generated by the sinoatrial node activates the atrioventricular node. The atrioventricular node briefly delays the propagation of the depolarization signal, allowing the atria to drain, before passing the depolarization signal to the ventricles of the heart. The coordinated contraction of both ventricles drives the flow of blood through the torso of a patient. In certain circumstances, the conduction of the depolarization signal from the atrioventricular node to the left and right ventricles may be interrupted or slowed. This may result in a dyssynchrony in the contraction of the left and right ventricles, which may lead to heart failure or death.

Cardiac Resynchronization Therapy (CRT) may correct the symptoms of electrical dyssynchrony by providing pacing therapy to one or both ventricles or atria, e.g., by providing pacing to encourage earlier activation of the left or right ventricles. By pacing the contraction of the ventricles, the ventricles may be controlled so that the ventricles contract in synchrony. Some patients undergoing CRT have experienced improved ejection fraction, increased exercise capacity, and an improved feeling of well-being.

Providing CRT to a patient may involve determining whether the patient will derive benefit from the CRT prior to implantation of a cardiac rhythm device, determining optimal site for placement of one or more ventricular pacing leads, and programming of device parameters, such as selection of electrodes on multi-polar right or left ventricular leads, as well as selection of the timing of the pacing pulses delivered to the electrodes, such as atrioventricular (A-V) and intra-ventricular (V-V) delays. Assessment of electrical dyssynchrony for these purposes has typically involved clinically assessing QRS duration. Though CRT is recommended typically for patients with wide QRS duration, hemodynamic improvements through CRT have been reported in narrow QRS heart failure patients. Thus, some patients who may benefit from CRT may not be prescribed CRT based on present electrical dyssynchrony evaluation techniques. It is desirable to develop additional methods or systems that perform a noninvasive assessment of cardiac electrical dyssynchrony in order to identify patients who are able to benefit from CRT.

DETAILED DESCRIPTION

The present disclosure provides methods depicted in flow diagrams 13 and 14 and/or systems that can assess cardiac electrical dyssynchrony through a noninvasive ECG belt or array. The functional electrical metrics are derived from measurements of a cardiac cycle taken from an array of surface electrodes. In one or more embodiments, the array can be one or more rows of electrodes on a front portion of a torso in the upper to middle regions (i.e. around the nipple-line) and another row of electrodes on a posterior section of the torso.

Functional electrical metrics of electrical dyssynchrony and electrical activation patterns are used in a variety of cardiac resynchronization therapy (CRT) applications. For example, the functional electrical metrics can be used to obtain feedback on efficacy of cardiac resynchronization during implant, which may be helpful in determining an optimal placement of a medical electrical lead. Additionally, an optimal pacing vector can be selected by employing features of the present disclosure. CRT timing parameters (e.g. A-V delay, V-V delay) can also be optimized through evaluation of multisite pacing. Significantly, patient selection is also improved by determining which patients can potentially benefit from CRT pacing. For example, non-tachycardia patients may benefit from CRT pacing as implemented herein.

One or more embodiments of cardiac pacing are disclosed herein. In one or more embodiments, a baseline rhythm is determined using a plurality of body-surface electrodes. Thereafter, a set of baseline functional electrical metrics is determined. Resynchronization pacing is delivered using a right ventricular electrode and a pacing left ventricular electrode or only pacing with a left ventricular electrode. A set of functional electrical metrics relating to cardiac depolarization and repolarization is determined in response to resynchronization pacing. A determination is then made as to whether relative reduction of at least one functional electrical metric from the set of functional electrical metrics exceeds X % of its corresponding value from the set of baseline functional electrical metrics. A determination is then made as to whether an absolute value of at least one electrical metric from the set of the functional electrical metrics is less than Y ms. A determination is then made as to whether a site is responsive to cardiac resynchronization therapy (CRT) based upon the functional electrical metric data compared to the baseline.

Figure 1:
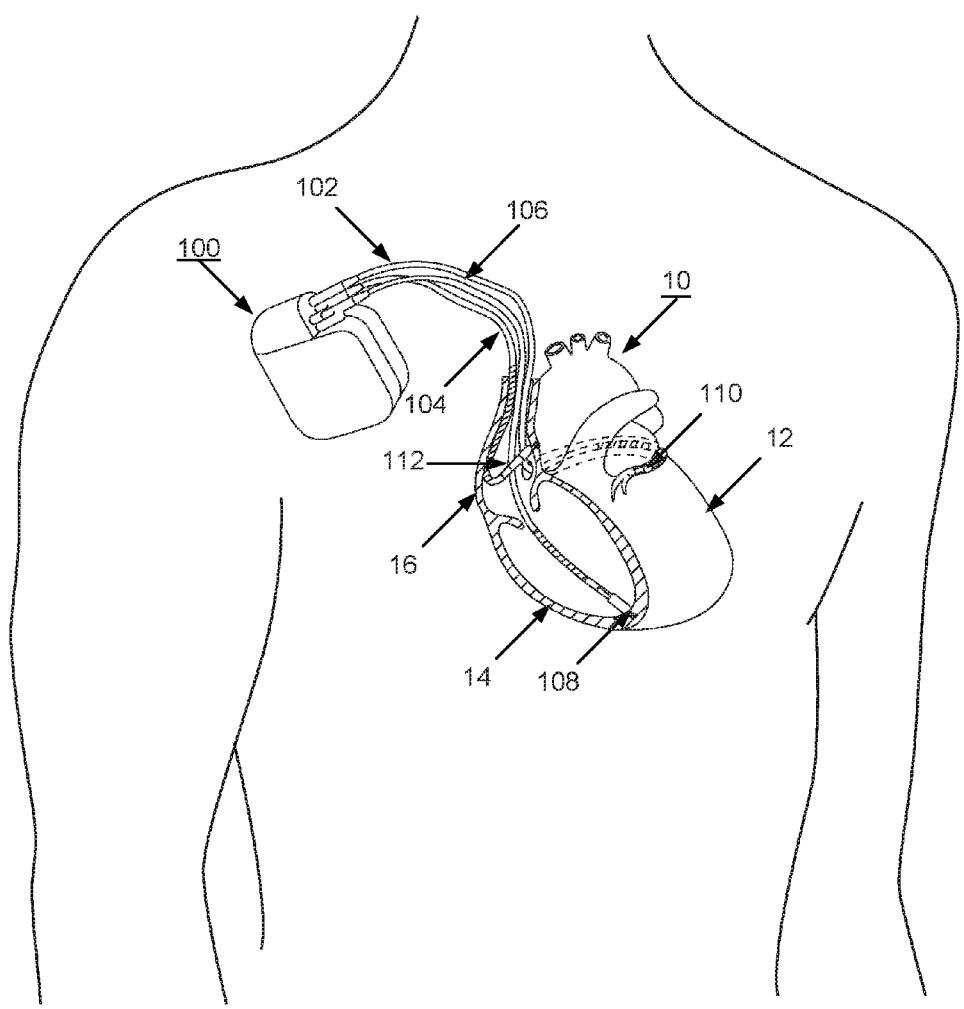
FIG. 1 is a conceptual diagram illustrating an example system that may be used to provide CRT to a heart of a patient.

FIG. 1 is a conceptual diagram illustrating an example system that may be used to provide CRT to heart 10 of patient 1. The system may include an implantable medical device (IMD) 100. IMD 100 may be a CRT pacemaker or CRT defibrillator. IMD 100 may be equipped with one or more leads; leads 102, 104, and 106; that are inserted into or on the surface of the left ventricle 12, right ventricle 14, or right atrium 16 of heart 10. Leads 102, 104, and 106 may be equipped with one or more electrodes 108, 110, and 112.

A heart 10 may suffer from electrical dyssynchrony. Electrical dyssynchrony may occur when the depolarization signals that start the contraction of ventricles 12 and 14 do not reach the ventricles in a coordinated manner, and results in an inefficient pumping action of heart 10. Patient 1 may experience symptoms of heart failure. Electrical dyssynchrony may be caused by damage to the electrical system of heart 10, e.g., a bundle branch block or damage to the fascicle of heart 10. Alternate conduction pathways may form within heart 10, but these pathways may slow the progress of the electrical depolarization signal and result in the asynchronous contraction of ventricles 12 and 14.

IMD 100 provides CRT stimulation to heart 10 of patient 1. IMD 100 is depicted as being configured to deliver stimulation to right atrium 16, right ventricle 14, and left ventricle 12 of heart 10. In other examples, IMD 100 may be configured to deliver stimulation to other portions of heart 10 depending on the condition of patient 1. IMD 100 may interact with an external programmer (not shown) to adjust operating characteristics, such as A-V and V-V delays, of the therapy delivered by IMD 100. In some examples, IMD 100 may also be configured to sense the electrical activity of heart 10 through the electrodes on one or more of leads 102, 104, and 106.

As shown in FIG. 1, leads 102, 104, 106 may extend into the heart 10 of patient 1 to deliver electrical stimulation to heart 10 and synchronize the contraction of ventricles 12 and 14. Right ventricular lead 106 extends through one or more veins (not shown), the superior vena cava (not shown), and right atrium 16, and into right ventricle 14. Left ventricular coronary sinus lead 102 extends through one or more veins, the vena cava, right atrium 16, and into the coronary sinus (not shown) to a region adjacent to the free wall of left ventricle 12 of heart 10. Right atrial lead 104 extends through one or more veins and the vena cava, and into the right atrium 16 of heart 10.

In other configurations, IMD 100 may be equipped with more or fewer leads, depending on the requirements of the therapy provided to patient 1. For example, IMD 100 may be equipped with leads that extend to greater or fewer chambers of heart 10. In some examples, IMD 100 may be equipped with multiple leads that extend to a common chamber of heart, e.g., multiple leads extending to the left ventricle 12. IMD 100 may also be equipped with one or more leads that are placed on the heart through other means providing access to the cardiac tissue, such as surgical epicardial lead placement, and other pericardial access approaches. In some examples, IMD 100 may be equipped with a left ventricular lead that is placed on the heart endocardially. Additionally, although illustrated as implanted on the right side of patient 1 in FIG. 1, IMD 100 may in other examples be implanted on the left side of the pectoral region of the patient, or within the abdomen of the patient.

Electrodes 108, 110, and 112 may attach to portions of heart 10 to provide electrical stimulation or sense the electrical depolarization and repolarization signals of heart 10. Electrode 108, in right ventricle 14, may be affixed to the wall of heart 10 via a screw based mechanism. Electrode 110 may comprise multiple electrodes mounted the same lead, allowing lead 102 to both transmit therapeutic shocks as well as electrical sense data detected by electrode 110. Electrodes 110 and 112 may be attached to the surface of heart 10 via glue, barbs, or another permanent or semi-permanent attachment mechanism.

Figure 2:
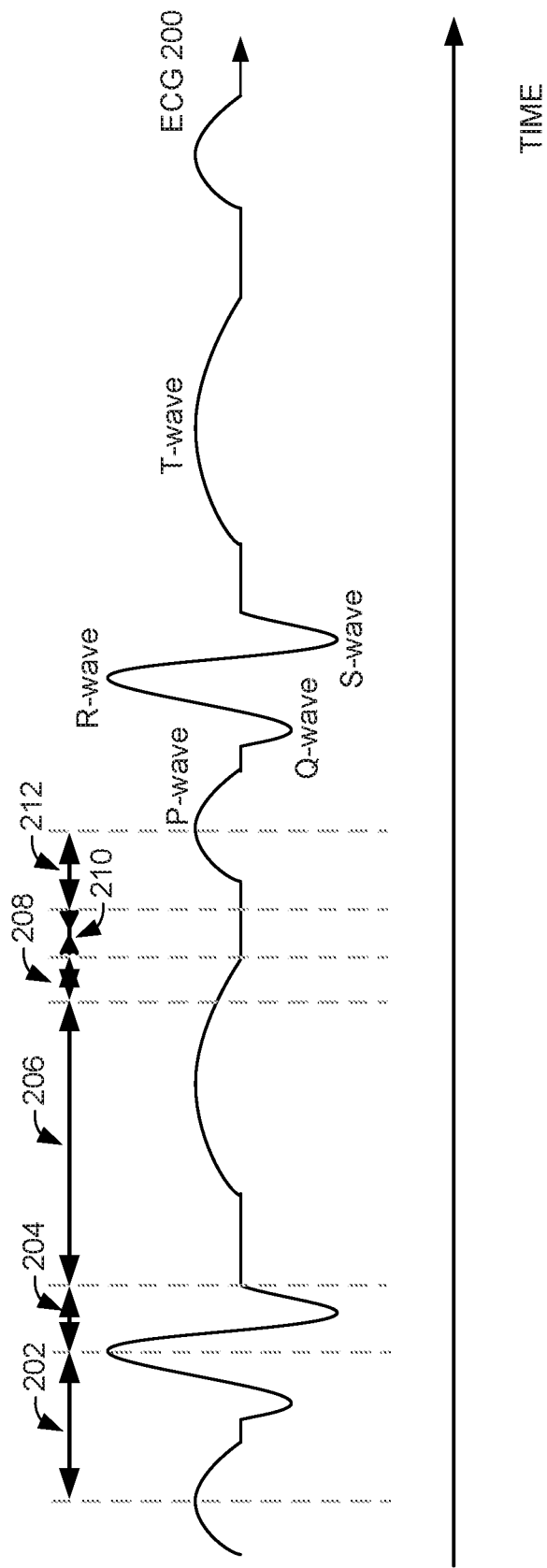
FIG. 2 is a timing diagram showing an example ECG tracing of two healthy heart beats.
Figure 3:
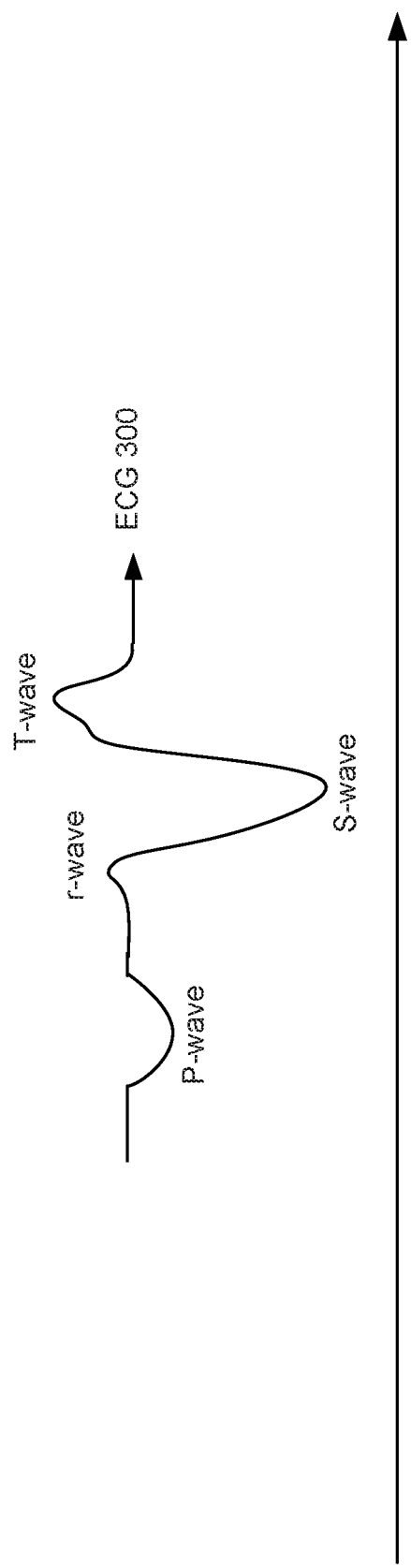
FIG. 3 is a timing diagram showing an example ECG tracing of a patient suffering from left bundle branch block.

FIGS. 2 and 3 contrast timing diagrams from a healthy heart (FIG. 2) and a heart experiencing electrical dyssynchrony (FIG. 3). The timing diagram of FIG. 2 shows an example ECG tracing 200 in conjunction with certain periods or phases of the mechanical cardiac cycle. The depiction and associated description of FIG. 2 are generalized in the sense that the relationship between the timing of electrical and mechanical events is not necessarily as described for all subjects, or at all times for any given subject.

ECG tracing 200 depicts the electrical signal of two example healthy cardiac cycles. The electrical signal of a healthy heart comprises a series of 5 characteristic waves: the P-wave, Q-wave, R-wave, S-wave, and T-wave. Each of these waves, and the intervals between them, correspond to discrete events in the functioning of a healthy heart.

In general, at some point during period 202, which stretches from the peak of a P-wave to the peak of the subsequent R-wave, atrial systole occurs, which is the contraction of the atria that drives blood from the atria into the ventricles. Period 204, from the peak of the R-wave to the opening of the aortic valve, generally marks a period of isovolumetric contraction. The atrioventricular and aortic valves are closed, preventing blood flow and leading to an increase in pressure in the ventricles but not yet in the aorta. Period 206, bounded by the opening and closing of the aortic valves is generally when ejection occurs during the cardiac cycle. During ejection period 206 the ventricles contract and empty of blood, driving the blood into cardiovascular system. As the contraction of the ventricles complete, the pressure of the blood within the cardiovascular system closes the aortic valves. Period 208, bounded by the closing of the aortic valves and the opening of the atrioventricular valves, is the isovolumetric relaxation of the ventricles. Periods 210 and 212 are collectively known as the late diastole, where the whole heart relaxes and the atria fill with blood. Period 210 corresponds to a rapid inflow of blood while period 212 corresponds to diastasis, the period of slower flow blood into the atria before the atrial systole 202 occurs again.

The P-wave marks the stimulation of the atria and the beginning of the cardiac cycle. The atria contract under the stimulation, forcing blood into the ventricles. The PR segment marks the delay as the depolarization signal travels from the atrioventricular node to the Purkinje fibers. The Q-wave marks the depolarization of the interventricular septum as an initial part of the depolarization of the ventricles. The R-wave follows the Q-wave and represents the depolarization of the ventricles. The S-wave follows the R-wave and represents the later depolarization of the ventricles. The T-wave marks the recovery and repolarization of the ventricles in preparation for the next beat of the heart.

The QRS complex, spanning from the beginning of the Q-wave to the end of the S-wave, represents the electrical activation of the myocardium. Ventricular contraction of both the left and right ventricles is in response to the electrical activation. The QRS complex typically lasts from 80 to 120 ms. The relatively large amplitude of the QRS complex is due to the large muscle mass of the ventricles. Issues affecting the synchrony of the ventricular contraction may be demonstrated in the deformation of the QRS complex. For example, electrical dyssynchrony in the contraction of the ventricles can widen the R-wave or produce two R-wave peaks, typically labeled the r-wave and R'-wave, corresponding to the depolarization of each ventricle. The S-wave and the T-wave may be morphological different than in an ECG tracing of a healthy heart.

FIG. 3 is a timing diagram showing ECG tracing 300. ECG tracing 300 depicts the electrical signal of a patient suffering from a left bundle branch block. A sign of the condition is the presence of an rS complex versus the typical QRS complex, though other variations of Q, R, and S waves form combinations that may be present in patients suffering from a left bundle branch block, right bundle branch blocks, or other ventricular conduction conditions. The extended duration of the rS complex indicates an extended ventricular contraction time, likely due to electrical dyssynchronies.

Diagnosis of a left or right bundle branch block, or cardiac electrical dyssynchrony in general, typically involves measuring the duration of the QRS complex (or other complex marking the depolarization of the ventricles). QRS complexes lasting 100 ms or longer may indicate a partial bundle branch block and 120 ms or longer a complete bundle branch block. In FIG. 3, the initial Q-wave is not visible, instead the tracing shows an initial r-wave, corresponding to the initial depolarization of the right ventricle and followed by an S-wave marking the rapid depolarization of both ventricles after the cardiac signal has reached the left ventricle after traveling through the myocardium of the heart, rather than through the bundle branches. Because the myocardium conducts electricity more slowly than the bundle branches, the entire complex is spread out over a longer period.

Absent a case of bundle branch block—such as the one shown in FIG. 3—or other condition, diagnosis may be more challenging. Occult dyssynchronies may be present that, while responsive to CRT, may not be readily identifiable from an examination of the typical 12-lead ECG. These occult dyssynchronies may manifest in the electrical signals generated by the heart and measured on the surface of the torso and may be diagnosable through alternative means of analysis, such as by determining cardiac activation times at a plurality of spatially distributed locations according to the techniques described herein.

Figure 4A:
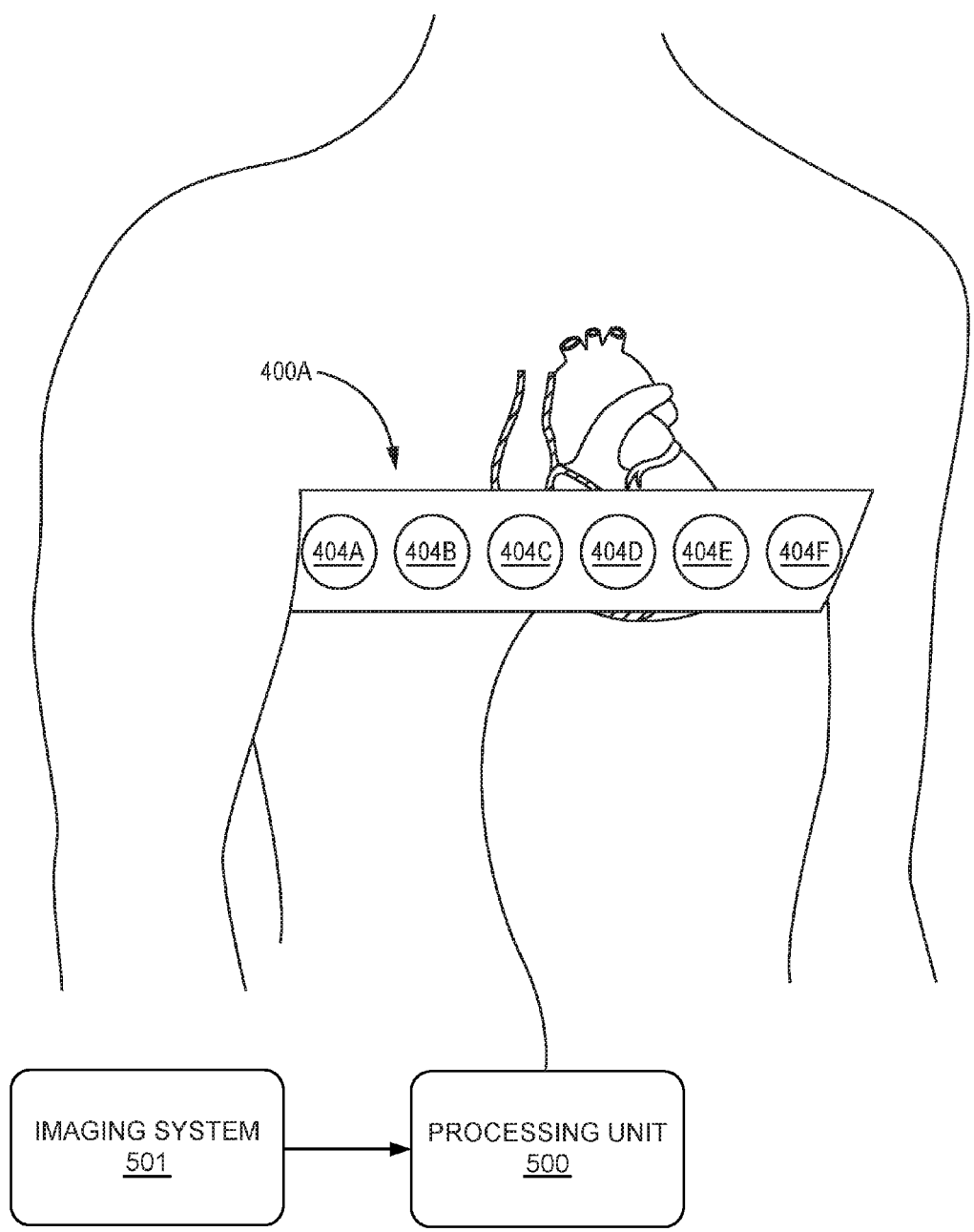
FIGS. 4A and 4B are conceptual diagrams illustrating example systems for measuring torso-surface potentials.
Figure 4B:
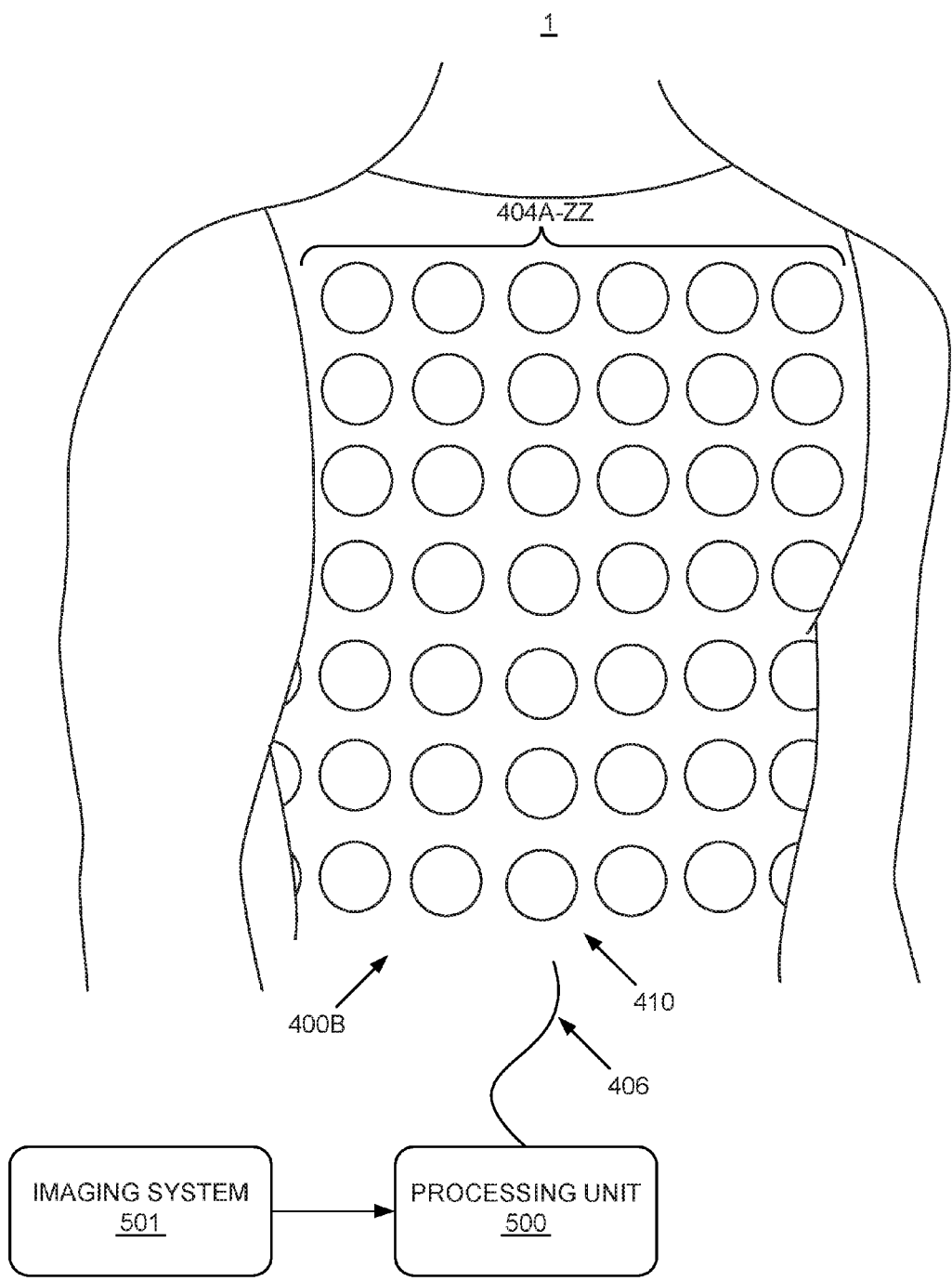

FIGS. 4A and 4B are conceptual diagrams illustrating example systems for measuring body-surface potentials and, more particularly, torso-surface potentials. In one example illustrated in FIG. 4A, sensing device 400A, comprising a set of electrodes 404A-F (generically "electrodes 404") and strap 408, is wrapped around the torso of patient 1 such that the electrodes surround heart 10.

As illustrated in FIG. 4A, electrodes 404 may be positioned around the circumference of patient 1, including the posterior, lateral, and anterior surfaces of the torso of patient 1. In other examples, electrodes 404 may be positioned on any one or more of the posterior, lateral, and anterior surfaces of the torso. Electrodes 404 may be electrically connected to processing unit 500 via wired connection 406. Some configurations may use a wireless connection to transmit the signals sensed by electrodes 404 to processing unit 500, e.g., as channels of data.

Although in the example of FIG. 4A sensing device 400A comprises strap 408, in other examples any of a variety of mechanisms, e.g., tape or adhesives, may be employed to aid in the spacing and placement of electrodes 404. In some examples, strap 408 may comprise an elastic band, strip of tape, or cloth. In some examples, electrodes 404 may be placed individually on the torso of patient 1.

Electrodes 404 may surround heart 10 of patient 1 and record the electrical signals associated with the depolarization and repolarization of heart 10 after the signals have propagated through the torso of patient 1. Each of electrodes 404 may be used in a unipolar configuration to sense the torso-surface potentials that reflect the cardiac signals. Processing unit 500 may also be coupled to a return or indifferent electrode (not shown) which may be used in combination with each of electrodes 404 for unipolar sensing. In some examples, there may be 12 to 16 electrodes 404 spatially distributed around the torso of patient 1. Other configurations may have more or fewer electrodes 404.

Processing unit 500 may record and analyze the torso-surface potential signals sensed by electrodes 404. As described herein, processing unit 500 may be configured to provide an output to a user indicating the electrical dyssynchrony in heart 10 of patient 1. The user may make a diagnosis, prescribe CRT, position therapy devices, e.g., leads, or adjust or select treatment parameters based on the indicated electrical dyssynchrony.

In some examples, the analysis of the torso-surface potential signals by processing unit 500 may take into consideration the location of electrodes 404 on the surface of the torso of patient 1. In such examples, processing unit 500 may be communicatively coupled to an imaging device 501, which may provide an image that allows processing unit 500 to determine coordinate locations of each of electrodes 400 on the surface of patient 1. Electrodes 404 may be visible, or made transparent through the inclusion or removal of certain materials or elements, in the image provided by imaging system 501.

FIG. 4B illustrates an example configuration of a system that may be used to evaluate electrical dyssynchrony in heart 10 of patient 1. The system comprises a sensing device 400B, which may comprise vest 410 and electrodes 404 A-ZZ (generically "electrodes 404"), a processing unit 500, and imaging system 501. Processing unit 500 and imaging system 501 may perform substantially as described above with respect to FIG. 4A. As illustrated in FIG. 4B, electrodes 404 are distributed over the torso of patient 1, including the anterior, lateral, and posterior surfaces of the torso of patient 1.

Sensing device 400B may comprise a fabric vest 410 with electrodes 404 attached to the fabric. Sensing device 400B may maintain the position and spacing of electrodes 404 on the torso of patient 1. Sensing device 400B may be marked to assist in determining the location of electrodes 404 on the surface of the torso of patient 1. In some examples, there may be 150 to 256 electrodes 404 distributed around the torso of patient 1 using sensing device 400B, though other configurations may have more or fewer electrodes 404.

Figure 5:
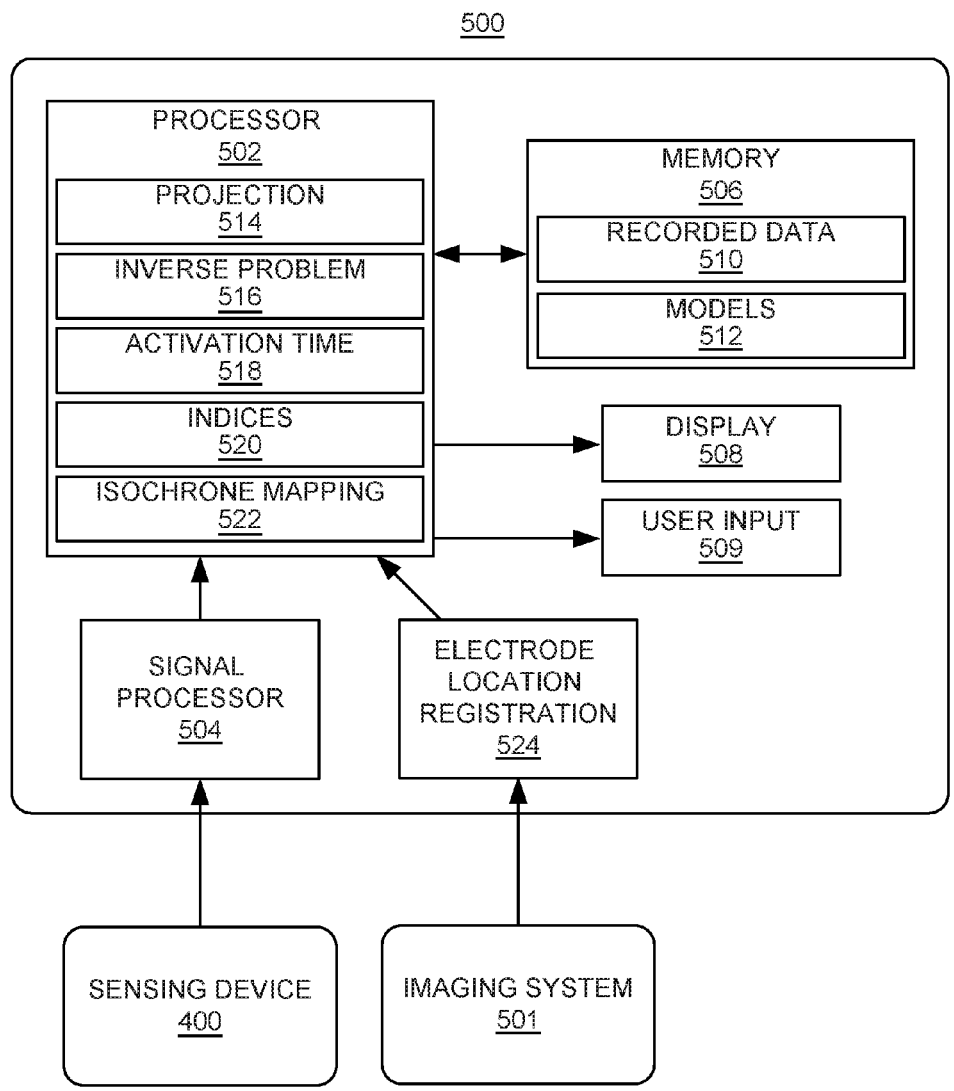
FIG. 5 is a block diagram illustrating an example system for measuring torso-surface potentials.

FIG. 5 is a block diagram illustrating an example system for measuring torso-surface potentials and providing indications of electrical dyssynchrony. The example system may comprise a processing unit 500 and a set of electrodes 404 on a sensing device 400, e.g., one of example sensing devices 400A or 400B (FIGS. 4A and 4B). The system may also include an imaging system 501.

As illustrated in FIG. 5, processing unit 500 may comprise a processor 502, signal processor 504, memory 506, display 508, and user input device 509. Processing unit 500 may also include an electrode location registration module 524. In the illustrated example, processor 502 comprises a number of modules and, more particularly, a projection module 514, an inverse problem module 516, an activation time module 518, an indices module 520, and an isochrones mapping module 522. Memory 506 may store recorded data 510 and models 512.

Processing unit 500 may comprise one or more computing devices, which may be co-located, or dispersed at various locations. The various modules of processing unit 500, e.g., processor 502, projection module 514, inverse problem module 516, activation time module 518, statistics module 520, isochrones mapping module 522, signal processor 504, electrode location registration module 524, display 508, memory 506, recorded data 510 and torso models 512 may be implemented in one or more computing devices, which may be co-located, or dispersed at various locations. Processor 502, and the modules of processor 502, may be implemented in one or more processors, e.g., microprocessors, of one or more computing devices, as software modules executed by the processor(s). Electrode location registration module 524 may, in some examples, be implemented in imaging system 501.

In addition to the various data described herein, memory 506 may comprise program instructions that, when executed by a programmable processor, e.g., processor 502, cause the processor and any components thereof to provide the functionality attributed to a processor and processing unit herein. Memory 506 may include any volatile, non-volatile, magnetic, optical, or electrical media, such as a hard disk, magnetic tape, random access memory (RAM), read-only memory (ROM), CD-ROM, non-volatile RAM (NVRAM), electrically-erasable programmable ROM (EEPROM), flash memory, or any other digital or analog media. Memory 506 may comprise one or more co-located or distributed memories. Memory 506 may comprise a tangible article that acts as a non-transitory storage medium for data and program instructions.

The torso-surface potential signals sensed by electrodes 404 of sensing device 400 may be received by signal processor 504 of processing unit 500. Signal processor 504 may include an analog-to-digital converter to digitize the torso-surface potential signals. Signal processor 504 may also include various other components to filter or otherwise condition the digital signals for receipt by processor 502.

Electrode location registration module 524 may receive imaging data from imaging system 501. Electrode location registration module 524 analyzes the imaging data. In particular, electrode registration location module 524 identifies electrodes 404, or elements co-located with the electrodes that are more clearly visible via the imaging modality, within the images. Electrode location registration module 524 may further identify the locations of each of the electrodes on the surface of the patient and/or within a three-dimensional coordinate system. In some examples, the locations of electrodes 404 may be manually identified and registered with processing unit 500, e.g., by a user, via electrode registration module 524.

The imaging data may comprise data representing one or more images of patient 1 wearing electrodes 404, e.g., of a sensing device 400. In some examples, the images may be obtained before or during a medical procedure, e.g., a surgical procedure to implant a cardiac rhythm device and lead system for delivery of CRT.

In some examples, processor 502 may store the torso-surface potential signals, imaging data from imaging system, electrode location data from electrode location registration module, or any values disclosed herein that are derived by processing of such signals and data by processor 502, within memory 506 as recorded data 510. Each recorded torso-surface potential signal, or other values derived therefrom, may be associated with a location of the electrode 404 that sensed the torso-surface potential signal. In this manner, the torso-surface potential data may be correlated with the position of electrodes 404 on the torso of patient 1, or within a three-dimensional coordinate system, enabling spatial mapping of the data to particular locations on the surface of the torso or within the coordinate system. In some examples, aspects of the techniques described herein may be performed at some time after the acquisition of the torso-surface potential signals and location data based on recorded data 510.

Processor 502 may be configured to provide one or more indications of electrical dyssynchrony based on the torso-surface potential signals and, in some examples, the electrode location data. Example indications of electrical dyssynchrony include indices illustrating activation times for each electrode/location distributed about the torso or heart, or for one or more subsets of electrodes located within a common region, e.g., within a left posterior, left anterior, right posterior, or right anterior region. In some examples, processor 502 may be configured to provide a set of two or more different indications, e.g., several different indications, for each of two or more different regions, e.g., several different regions, of the torso or heart.

Some indications of dyssynchrony may include statistical values or other indices derived from activation times for each electrode location or one or more subsets of electrodes within one or more regions. Other examples indications of electrical dyssynchrony that may be determined based on activation times at various electrodes/locations include graphical indications, such as an isochrone or other activation maps, or an animation of electrical activation. Other examples indications of electrical dyssynchrony that may be determined based on activation times at various electrodes/locations include identifying one of a predetermined number of dyssynchrony levels, e.g., high, medium, or low, via text or color, e.g., red, yellow, green, for example.

In some examples, the various indications of dyssynchrony for one or more regions may be determined based on data collected at two or more different times and/or under two or more different conditions. For example, the various indications of dyssynchrony may be determined based on torso-potential signals collected during intrinsic conduction of heart 10, and also determined based on torso-potential signals collected during CRT. In this manner, the potential dyssynchrony-reducing benefit of CRT may be evaluated for the patient by comparing the different values, graphical representations, or the like, resulting from intrinsic conduction and CRT. As another example, the various indications of dyssynchrony may be determined each of a plurality of different times based on torso-potential signals collected during delivery of CRT with different lead positions, electrode configurations, or CRT parameters, e.g., A-V or V-V interval values. In this manner, the relative dyssynchrony-reducing benefits of the different lead positions, electrode configurations, or CRT parameters positions may be evaluated for the patient by comparing the different values, graphical representations, or the like.

Models 512 may include a plurality of different models, e.g., three-dimensional models, of the human torso and heart. A model torso or model heart may be constructed by manual or semi-automatic image segmentation from available databases of previously acquired medical images (CT/MRI) of a plurality of subjects, e.g., cardiomyopathy patients, different than patient 1, using commercially available software. Each model may be discretized using a boundary element method. A plurality of different torso models may be generated. The different models may represent different subject characteristics, such as different genders, disease states, physical characteristics (e.g., large frame, medium frame and small frame), and heart sizes (e.g., x-large, large, medium, small). By providing input via user input 509, a user may select from among the various model torsos and model hearts that may be stored as models 512 in memory 506, so that the user may more closely match the actual torso and heart 10 of patient 1 with the dimensions and geometry of a model torso and model heart. In some examples, medical images of the patient, e.g., CT or MRI images, may be manually or semi-automatically segmented, registered, and compared to models 512 for selection from amongst the models 512. Furthermore, single or multiple view 2-D medical images (e.g., x-ray, fluoroscopy) may be segmented or measured to determine approximate heart and torso dimensions specific to the patient in order to select the best fit model torso and heart.

Projection module 514 may project the locations of electrodes 404, e.g., stored as recorded data 510 within of memory 506, onto an appropriate, e.g., user-selected, model torso contained in model data module 512 of memory 506. By projecting the location of electrodes 404 onto the model torso, projection module 514 may also project the torso-surface potential signals of patient 1 sensed by electrodes 404 onto the model torso. In other examples, the measured electrical potentials may be interpolated and resamples at electrode positions given by the model. In some examples, projecting the torso-surface potentials onto the model torso may allow processor 502, via inverse problem module 516, to estimate the electrical activity of at various locations or regions of the model heart corresponding to heart 10 of patient 1 that produced the measured torso-surface potentials.

Inverse problem module 516 may be configured to solve the inverse problem of electrocardiography based on the projection of the measured torso-surface potentials, recorded by electrodes 404, onto the model torso. Solving the inverse problem of electrocardiography may involve the estimation of potentials or activation times in heart 10 based on a relationship between the torso and heart potentials. In one example method, model epicardial potentials are computed from model torso potentials assuming a source-less volume conductor between the model heart and the model torso in an inverse Cauchy problem for Laplace's equation. In another example method, an analytic relationship between torso-surface potentials and the cardiac transmembrane potential is assumed. Torso-surface potentials may be simulated based on this relationship. In some examples, inverse problem module 516 may utilize techniques described by Ghosh et al. in "Accuracy of Quadratic Versus Linear Interpolation in Non-Invasive Electrocardiographic Imaging (ECGI)," Annals of Biomedical Engineering, Vol. 33, No. 9, September 2005, or in "Application of the L1-Norm Regularization to Epicardial Potential Solution of the Inverse Electrocardiography Problem," Annals of Biomedical Engineering, Vol. 37, No. 5, 2009, both of which are incorporated herein by reference in their entireties. In other examples, any known techniques for solving the inverse problem of electrocardiography may be employed by inverse problem module 516.

Activation time module 518 may compute the activation times directly from measured torso-surface potentials, or by estimating model transmembrane potentials. In either case, an activation time for each electrode/location may be determined as a time period between two events, such as between the QRS complex onset and the minimum derivative (or steepest negative slope) of the sensed torso potential signal or estimate epicardial potential signal. Thus, in one example, cardiac activation times are estimated from the steepest negative slope of the model epicardial electrograms. Cardiac activation times (parameters in the analytic relationship between torso-surface potential and cardiac transmembrane potential) may, in other configurations, be computed based on minimizing the least square difference between the measured torso-surface potentials and simulated torso-surface potentials. A color-coded isochrone map of ventricular, epicardial, or torso-surface activation times may be shown by display 308. In other examples, display 308 may show a two-color animation of propagation of the activation wavefront across the surface of the model heart or the torso-surface.

Indices module 520 may be configured to compute one or more indices of electrical dyssynchrony from the torso-surface or cardiac activation times. These indices may aid in the determination of whether the patient is a candidate for CRT, placement of CRT leads, and selection of CRT parameters. For example, LV lead 102 (FIG. 1) may be positioned at the site that reduces dyssynchrony from one or more indices or, alternatively, the largest electrical resynchronization as demonstrated by the indices. The same indices may be also used for programming A-V and/or V-V delays during follow-up. As indicated above, the indices may be determined based on the activation times for all electrodes/locations, or for one or more subsets of electrodes in one or more regions, e.g., to facilitate comparison or isolation of a region, such as the posterior and/or left anterior, or left ventricular region.

One of the indices of electrical dyssynchrony may be a standard deviation index computed as the standard deviation of the activations-times (SDAT) of some or all of electrodes 404 on the surface of the torso of patient 1. In some examples, the SDAT may be calculated using the estimated cardiac activation times over the surface of a model heart.

A second example index of electrical dyssynchrony is a range of activation times (RAT) which may be computed as the difference between the maximum and the minimum torso-surface or cardiac activation times, e.g., overall, or for a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart 10 have been delayed in activation. In some examples, the RAT may be calculated using the estimated cardiac activation times over the surface of a model heart.

A third example index of electrical dyssynchrony estimates the percentage of electrodes 404 located within a particular region of interest for the torso or heart, whose associated activation times are greater than a certain percentile, for example the 70th percentile, of measured QRS complex duration or the determined activation times for electrodes 404. The region of interest may be a posterior, left anterior, and/or left-ventricular region, as examples. This index, the percentage of late activation (PLAT), provides an estimate of percentage of the region of interest, e.g., posterior and left-anterior area associated with the left ventricular area of heart 10, which activates late. A large value for PLAT may imply delayed activation of substantial portion of the region, e.g., the left ventricle 12 (FIG. 1), and the potential benefit of electrical resynchronization through CRT by pre-exciting the late region, e.g., of left ventricle 12. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

Isochrone module 522 may be configured to generate an isochrone map depicting the dispersion of activation times over the surface of the torso of patient 1 or a model heart. Isochrone module 522 may incorporate changes in the torso-surface or cardiac activation times in near real-time, which may permit near instant feedback as a user adjusts a CRT device or monitors patient 1 to determine if CRT is appropriate. Isochrone maps generated by isochrone module 522 may be presented to the user via display 508.

In general, processor 502 may generate a variety of images or signals for display to a user via display 508 based on the measured torso-surface potentials, calculated torso-surface or estimated cardiac activation times, or the degree of change in electrical dyssynchrony. For example, a graded response reflecting the efficacy of a particular location of the LV lead 102 during biventricular pacing or single ventricle fusion pacing may be provided to the physician in terms of a red, yellow and green signal. A red signal may be shown if the reduction in electrical dyssynchrony during CRT pacing compared to intrinsic rhythm is negative (an increase in electrical dyssynchrony) or minimal, e.g., less than 5%. CRT pacing includes biventricular pacing or fusion pacing described, for example, in application Ser. No. 13/464,228, and Ser. No. 13/772,890 filed on May 4, 2012 and Feb. 21, 2013, respectively and incorporated by reference herein, in their entirety. A yellow signal may be triggered if there is some reduction in electrical dyssynchrony during CRT pacing compared to intrinsic rhythm, for example between 5% and 15%, but there may be potentially better sites for lead placement. If the reduction in electrical dyssynchrony during CRT pacing compared to intrinsic rhythm is substantial, e.g., greater than 15%, a green signal may be triggered indicating to the physician that the present site provides effective changes in synchronization. The feedback from this system in combination with other criteria (like magnitude of pacing threshold, impedance, battery life, phrenic nerve stimulation) may be also used to choose an optimal pacing vector for one or more multipolar leads. The feedback from this system may be also used for selecting optimal device timings (A-V delay, V-V delay, etc) influencing the extent of fusion of intrinsic activation with paced activation from single or multiple ventricular sites, or discerning acute benefit of single site fusion pacing versus multi-site pacing and choice of appropriate pacing type.

Display 508 may also display three-dimensional maps of electrical activity over the surface of the torso of patient 1 or over a model heart. These maps may be isochrone maps showing regions of synchronous electrical activity as the depolarization progresses through heart 10 of patient 1. Such information may be useful to a practitioner in diagnosing asynchronous electrical activity and developing an appropriate treatment, as well as evaluating the effectiveness of the treatment.

Figure 6:
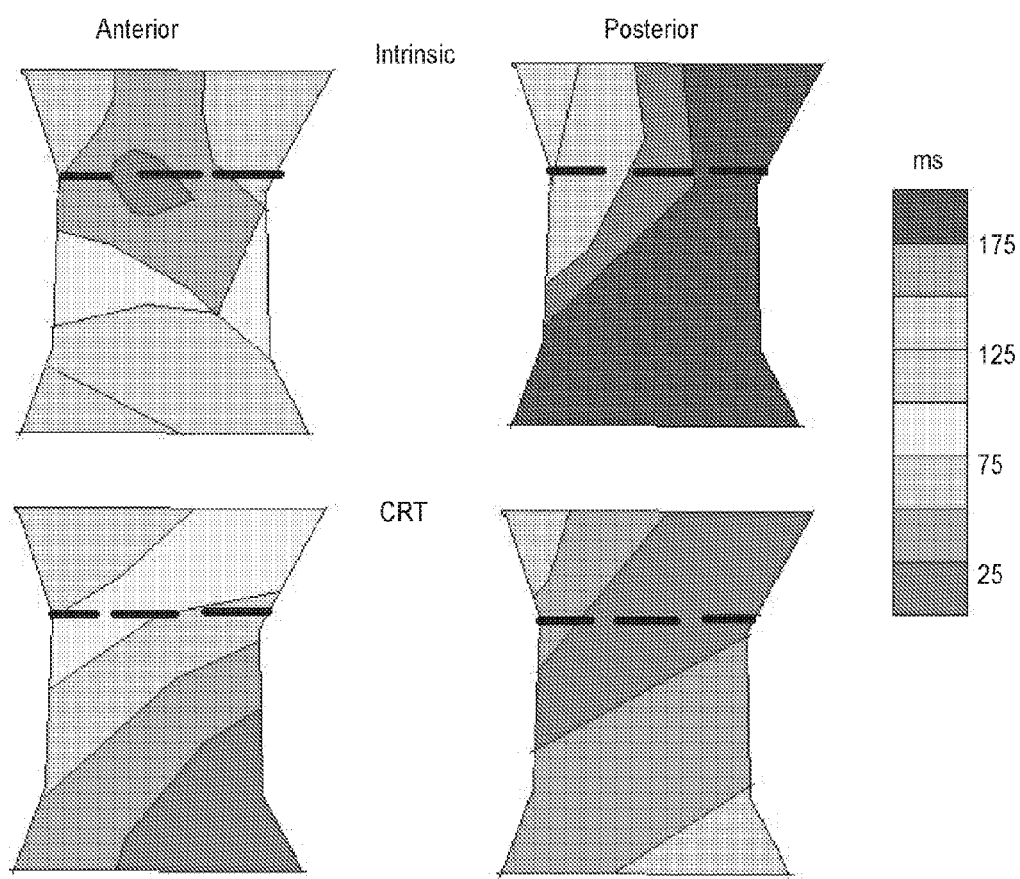
FIG. 6 is a series of simulated isochrone maps of torso-surface activation times for typical left bundle branch block intrinsic rhythm and CRT pacing.

FIG. 6 is a series of simulated isochrone maps 600 of torso-surface activation times over the torso of a patient suffering from an electrical dyssynchrony in the left ventricle before and during treatment with a CRT device. The isochrone maps before (intrinsic) and after treatment are divided into two views: anterior and posterior. Line 602 represents the location of a subset of electrodes 404, e.g., a subset of electrodes 404 of sensing device 400B, that may be used to calculate one or more indices of electrical dyssynchrony. In some examples, line 602 may represent electrodes 404 on sensing device 400A.

The isochrone maps 600 of the natural and CRT assisted torso-surface activation times may be generated using multiple electrodes 404 distributed over the surface of the torso of a patient, e.g., using sensing device 400B. Generation of the isochrone maps 600 may include determining the location of electrodes 404, and sensing torso-surface potential signals with the electrodes. Generation of the isochrone maps 600 may further include calculating the torso-surface activation time for each electrode or electrode location by determining the point in the recorded QRS complex of the signal sensed by the electrodes corresponding to the maximum negative slope. In other examples, the torso-surface activation times may be determined by identifying the minimum derivative of the QRS complex. The measured torso-surface activation times may then be standardized and an isochrone map of the surface of the torso of the patient generated.

The delayed activation of certain locations associated with certain ones of electrodes 404 due to the electrical dyssynchrony is apparent in the posterior views of the intrinsic torso-surface activation times. Regions 604 indicate increased delay in the activation of the underlying heart. The corresponding posterior view during treatment with a CRT device indicate that regions 606, the same location as regions 604 on the maps of intrinsic torso-surface activation times, exhibits increased synchrony in electrical ventricular activity. The CRT maps exhibit decreased range and a lower standard deviation of torso-surface activation times. Further, the posterior regions no longer exhibit delayed activation times. The isochrone map of the torso-surface activation times during intrinsic and CRT pacing and changes in distribution of activation-times from intrinsic to CRT pacing may be used for diagnostic purposes or the adjustment of a CRT device.

One or more indices of electrical dyssynchrony may also be calculated from the torso-surface activation times used to generate isochrone maps 600. For example, SDAT, an indication of the spread of the activation times, for the patient's intrinsic heart rhythm using the complete set of electrodes 404 is 64. Using the reduced lead set marked by line 602 results in an SDAT of 62. The RAT for the intrinsic heart rhythm and complete lead set is 166.5 while the reduced lead set has a RAT of 160. PLAT for the intrinsic heart rhythm using the reduced and complete lead sets are 56.15% and 66.67%, respectively. This indicates that using a reduced lead set that circumscribes the heart of the patient, e.g., sensing device 400A and associated electrodes 404, may provide comparable indices of electrical dyssynchrony compared to using an electrode set covering the torso of the patient, such as sensing device 400B.

The indices of electrical dyssynchrony also provide indication of the effectiveness of the CRT device, with the SDAT for the reduced set of electrodes declining to 24, the RAT to 70 and PLAT to 36%. This indicates that the torso-surface activation times during CRT treatment were more narrowly distributed and in a smaller range than in the normal heart rhythm and that the percentage of electrodes 404 located on the left anterior surface of the torso of the patient registering late activation times decreased markedly.

Figure 7:
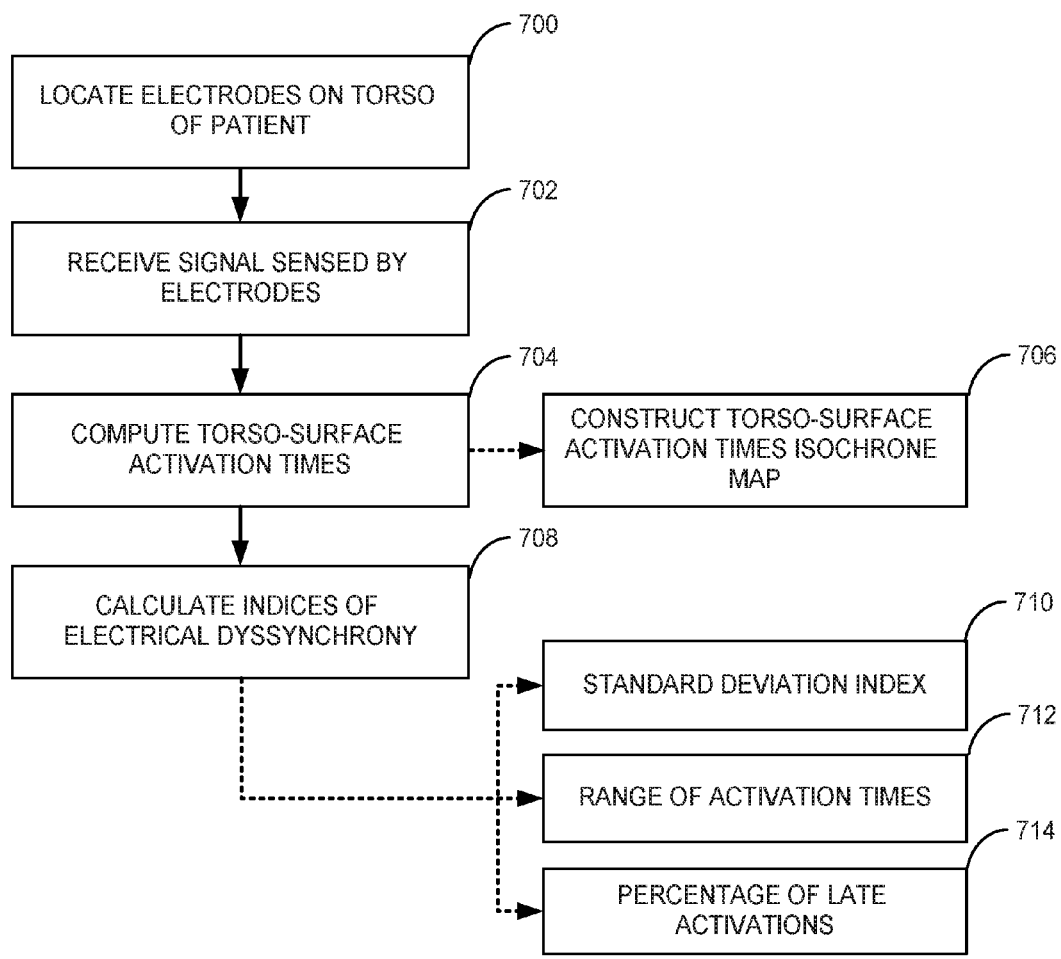
FIG. 7 is a flow diagram illustrating an example operation of a system to provide indications of the cardiac electrical dyssynchrony of a patient based on torso-surface activation times.

FIG. 7 is a flow diagram illustrating an example operation of a system to evaluate the cardiac electrical dyssynchrony of a patient via the torso-surface activation times. The location of electrodes, e.g., electrodes 404 (FIGS. 4A and 4B), distributed over the surface of the torso of the patient may be determined (700). A cardiac event, e.g., a depolarization, may generate an electrical signal that propagates through the torso of a patient, e.g., patient 1 (FIG. 1) and registers on the electrodes. The signal sensed by the electrodes may be received (702), e.g., by processing unit 500 (FIG. 5). The processing unit may calculate the torso-surface activation times (704). In some examples, the processing unit may also construct a torso-surface activation times isochrone map (706). The processing unit may also calculate at least one index of cardiac electrical dyssynchrony (708). These indices may comprise one or more of the SDAT (710), RAT (712), and the PLAT (714).

A cardiac event, such as a depolarization, generates an electrical signal that propagates through the torso. The electrical signal may comprise a QRS complex, or a variant caused by a heart related condition such as a left or right bundle branch block. The electrical signal may not propagate uniformly through the torso of a patient due to variations in conductivity within the torso and the heart. These delays may manifest in electrodes distributed over the surface of the torso of the patient registering the same electrical signal at different points in time.

The electrical signal generated by the cardiac event may register on the plurality of electrodes distributed over the surface of the torso of patient. The electrodes may be distributed over the anterior, lateral, and/or posterior surfaces of the torso, allowing the generation of a three-dimensional picture of the electrical activity occurring within the torso. In some examples, the electrodes may be placed to provide extensive coverage both above and below the heart, e.g., by using sensing device 400B (FIG. 4B). In other examples, a reduced set of electrodes may be arranged around the circumference of the torso, circumscribing the heart of the patient, e.g., using sensing device 400A (FIG. 4A). The electrodes may receive the complete waveform of the electrical signal generated by the cardiac event, and transmit the signal to a processing unit.

The location of electrodes distributed over the surface of the torso of the patient may be determined (700). Locating the electrodes may be performed automatically, e.g. by imaging system 501 and electrode location registration module 524 of processing unit 500 (FIG. 5). The electrodes may be located by analyzing one or more images of the torso of a patient and performing a pattern matching routine, e.g., recognizing the shape of an electrode against the torso of the patient, and storing the location of the electrode on the torso of the patient in processing unit memory. In other examples, the location of sensing device 400A or 400B may be determined and the locations of the electrodes determined based on the position of the sensing device, e.g., basing the position of the electrode on the patient through the known position of the electrode on the sensing device. In another example, the position of the electrodes may be measured manually.

The processing unit may receive the electrical signal from the electrodes and record the output in memory (702). The processing unit may record the raw output, e.g., the raw ECG tracing from each electrode, as well as location data for the electrodes, allowing the electrical signals detected by the electrodes to be mapped onto the surface of the torso of the patient.

The processing unit may compute the torso-surface activation times (704). A processor, e.g., processor 502 of processing unit 500 (FIG. 5), may retrieve ECG tracing data stored within the processing unit memory and analyze the tracing to detect depolarization of the ventricles of the heart, typically marked by a QRS complex in the tracing. The processor may, in some examples, detect ventricular depolarization by determining the time of the minimum derivative (or steepest negative slope) within the QRS complex measured with respect to the time of QRS complex onset. The determination of the activation time may be made for each electrode and stored in the processing unit memory.

In some configurations, the processing unit may construct an isochrone map of the torso-surface activation times, allowing the user to visually inspect the propagation of the electrical signals of the heart after progression through the torso of the patient. The isochrone map may be constructed by dividing the range of measured torso-surface activation times into a series of sub-ranges. The location of each electrode on the surface of the torso of the patient may be graphically represented. Regions of electrodes whose measured activation times fall within the same sub-range may be represented by the same color on the graphical representation.

The processing unit may also calculate one or more indices of electrical dyssynchrony based on the torso-surface activation times (708). These indices may include the SDAT (710), RAT (712), and PLAT (714). In some examples, the PLAT may be determined as the percentage of posterior electrodes activating after a certain percentage of the QRS complex duration.

As discussed above, in some examples, the construction of a torso-surface activation times isochrone map (706), or other graphical representation of dyssynchrony, as well as the calculation of indices of electrical dyssynchrony (708), may be performed for a particular region of the torso based the signals received from electrodes (702) in such regions. Graphical representations and indices of electrical dyssynchrony may be determined for each of a plurality of regions based on the signals received from the electrodes for such regions. In some examples, the representations and indices for various regions may be presented together or compared.

Figure 8:
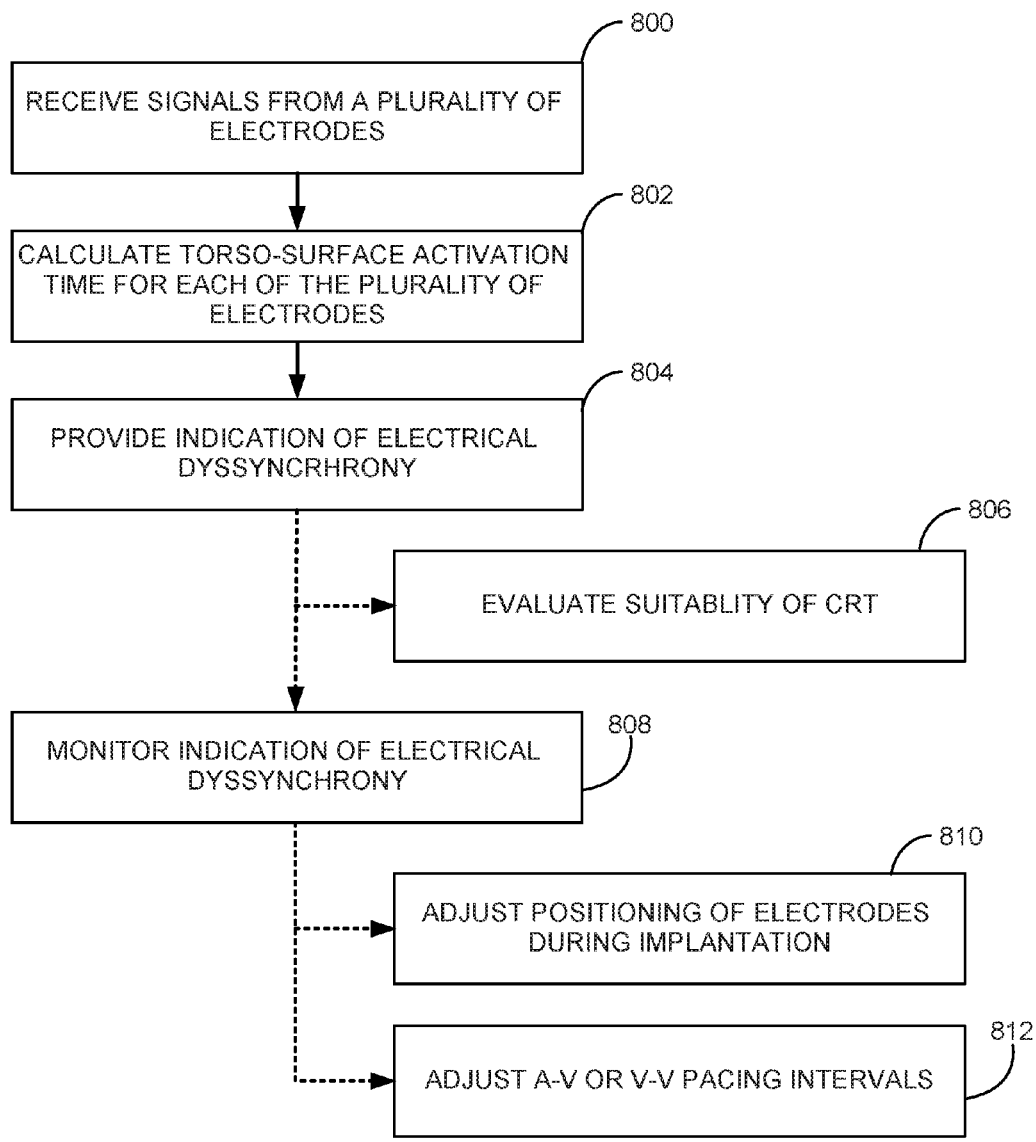
FIG. 8 is a flow diagram illustrating an example technique for prescribing and configuring CRT based on an assessment cardiac electrical dyssynchrony of a patient via the torso-surface activation times.

FIG. 8 is a flow diagram illustrating an example technique for measuring the cardiac electrical dyssynchrony of a patient via measured torso-surface activation times. A processing unit 500 may receive torso-surface potential signals from a plurality of electrodes (800), e.g., electrodes 404 (FIGS. 4A and 4B). The processing unit 500 may calculate the torso-surface activation times for each of the plurality of electrodes (802). The processing unit 500 may provide at least one indication of cardiac electrical dyssynchrony (804).

A user may evaluate whether a patient is a candidate for CRT based on the at least one indication of electrical dyssynchrony (806). The user may also monitor the at least one indication of electrical dyssynchrony (808), and use the changes in the at least one indication to aid in adjusting the positioning of electrodes, e.g., electrodes 108, 110, and 112 (FIG. 1), during implantation of a CRT device (810), e.g., IMD 100 (FIG. 1), or selection of the various programmable parameters, such as electrode combination and the A-V or V-V pacing intervals, of the CRT device (812), during implantation or a follow-up visit.

The various indications of cardiac electrical dyssynchrony described herein, such as statistical or other indices, or graphical representations of activation times, may indicate the presence of damage to electrical conductivity of the heart of the patient, for example the presence of a left or right bundle branch block, that may not be apparent from the examination of a standard 12-lead ECG readout. For example, a large SDAT indicates that the activation of the ventricles is occurring over a large time span, indicating that the depolarization of the ventricles is not occurring simultaneously. A large RAT also indicates a broad range of activation times and asynchronous contraction of the ventricles. A high PLAT indicates that a specific region of the heart, e.g., the posterior regions associated with the left ventricle, may be failing to activate in concert with the measured QRS complex. Additionally, by monitoring the at least one indication of cardiac electrical dyssynchrony, the user may detect changes in the electrical activity of the heart caused by different treatments or treatment configurations.

As described above, the various indications of electrical dyssynchrony, such as statistical indexes, may be calculated for each of a plurality of regions, e.g., posterior, left anterior, or the like, based on torso-surface activations times from the region. Additionally, evaluating whether a patient is a candidate for CRT based on the at least one indication of electrical dyssynchrony (806) may include determining the one or more indications of electrical dyssynchrony based on torso-surface activation times both during intrinsic conduction of the heart, and during CRT. Differences between the indications during intrinsic conduction and CRT may indicate that CRT would provide benefit for the patient, e.g., that the patient is a candidate for CRT. As described above, the user may also evaluate whether a patient is a candidate for CRT based on at least one indication of electrical dyssynchrony based on intrinsic rhythm alone. Furthermore, monitoring the at least one indication of electrical dyssynchrony (808) during implantation or a follow-up visit may include determining the one or more indications of electrical dyssynchrony for each of a plurality of lead positions, electrode configurations, or other parameter values based on torso-surface activation times resulting from delivery of CRT at the positions, or with the electrode configurations or parameter values. In this manner, differences between dyssynchrony indications associated with various locations, electrode configurations, or parameter values may be compared to determine preferred locations, configurations, or values.

Figure 9:
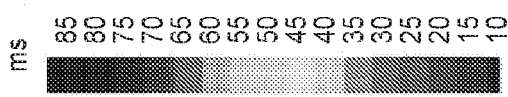
FIG. 9 is a series of isochrone maps of cardiac activation times constructed with two different heart-torso models using body-surface ECG data from the same patient.
Figure 9:
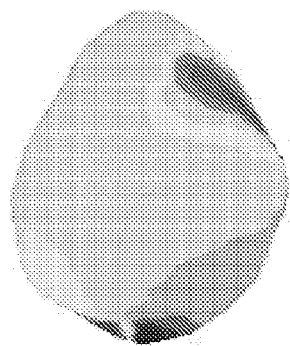
Figure 9:
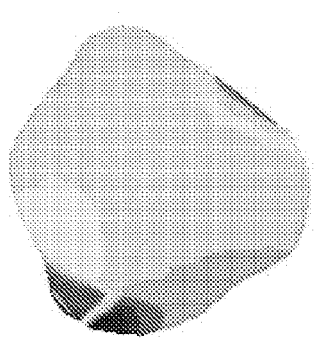
Figure 9:
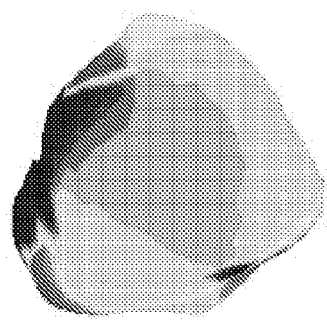
Figure 9:
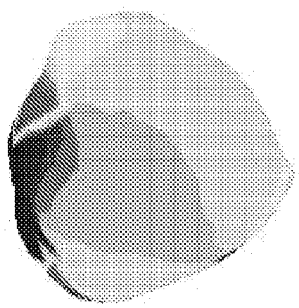
Figure 9:
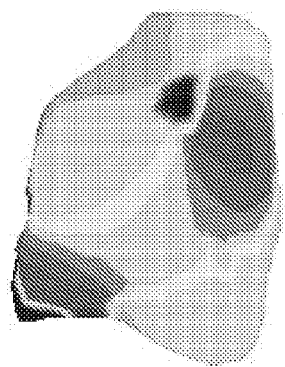
Figure 9:
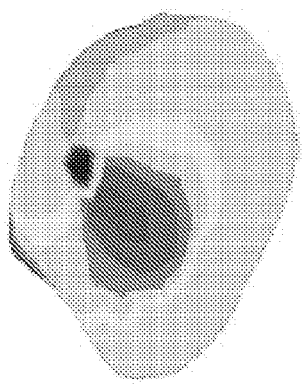

FIG. 9 is a series of isochrone maps of cardiac activation times. Views 900, 902 and 904 were constructed using torso-surface potentials measured on the surface of the torso of a patient and projected onto three dimensional models of the torso and the heart of the patient. Views 910, 912, and 914 were constructed using the measured torso-surface potentials of the same patient projected onto a different model torso and model heart.

The three-dimensional representation of the hearts depicted in views 900, 902, 904, 910, 912 and 914 were constructed using computer tomography (CT) images of hearts obtained from databases of previously acquired cardiothoracic images. The locations of the electrodes, e.g., electrodes 404 of sensing device 400B (FIG. 4B), on the torso of the patient may be plotted to approximate locations on a model torso. A computer may be used to solve the inverse problem of electrocardiography, which includes determining the electrical activity on the surface of the heart that would produce the measured torso-surface potentials. The isochrone maps illustrated in views 900, 902, 904, 910, 912 and 914 are based on images of hearts of two different patients, which are also used to determine the geometry of the heart and relationship to the corresponding torso for solving the inverse problem of electrocardiography.

The model torsos and hearts may be constructed by manual or semi-automatic image segmentation from available databases of previously acquired medical images (CT/MRI) of cardiomyopathy patients using commercially available software. Each model may be discretized using boundary element method and may be further manipulated to account for patients with different physical characteristics (e.g., large frame, medium frame and small frame) and heart sizes (e.g., x-large, large, medium, small).

A user may select the appropriate model torso and heart to suit the patient, e.g., a patient having a large torso may be simulated with a large frame model torso. In some examples, medical images of the patient, e.g., CT or MRI images, may be manually or semi-automatically segmented, registered, and compared to a variety of available models for selection from amongst the models. One or more views of 2-D medical images (e.g., X-ray or fluoroscopy) may also be used. The user may project the measured torso-surface potentials from the torso of the patient onto the corresponding locations on the model torso. The inverse problem of propagating the electrical signals from the model torso to the model heart may then be solved, and activation times for the model heart may be estimated.

In one example in which the techniques of this disclosure were applied, human thoracic CT images for other subjects were obtained from image databases. Semi-automatic image segmentation was performed on the images to generate the three-dimensional representation of the different models of hearts and torsos. In some examples, image segmentation may be done with the AMIRA software package commercially-available from Visage Imaging, Inc., of San Diego, Calif.

For the example, the projection of electrode locations on the patient torso to the model torso was approximate. In particular, the locations electrodes on the patient torso to the model torso the locations of the electrodes on the patient torso were projected onto the surface of the model torso based on the order in which the electrodes were mounted on the patient. For the purpose of this projection, the patient and model torsos were divided into right anterior, left anterior, right posterior and left posterior regions, using the sternum (anterior) and the spine (posterior) as references. Electrodes were arranged in vertical strips and three strips were applied to each region of the torso. Electrodes in these regions were projected on to the corresponding segments of the model torso. The method described is one of many techniques that may be used to registered or map the geometrical distribution of measured electrical potentials. For example, the measured electrical potentials. For example, the measured electrical potentials may be interpolated and resampled at electrode positions given by the model. Projection of the electrode locations from segments of the patient torso onto the corresponding segments of the model torso in the correct order enabled the activation patterns and spatial dispersion of activation on the model heart to reflect the activation patterns and spatial dispersion of activation on the actual patient heart with relative accuracy. In one example, the inverse problem of electrocardiography may be solved using the Matlab regularization toolbox (Hansen P C, Regularization Tools: A Matlab package for analysis and solution of discrete ill-posed problems, Numerical Algorithms, 6(1994), pp 1-35).

Input data-sets for solving the inverse problem consistent with the example may include multi-electrode surface ECG measurements, the 3-D Cartesian coordinates of the model heart and torso surfaces, and the mesh over each model surface which specified the connectivity of the different points on each surface. An output consistent with the techniques of this disclosure may include activation times on the 3-D model heart surface which can be visualized using visualization software and computer graphics tools. In some examples, the 3-D model heart surface may be visualized using the tools in Matlab (Mathworks Inc, Natick, Mass.) or more advanced visualization software, such as Tecplot (Tecplot Inc, Bellevue, Wash.).

Comparing estimated cardiac activation times on two different, both cardiac activation times determined from the same torso-surface potential signals for one subject, show similar patterns and distribution. For example, region 906 of views 902 and 904 corresponds in size and activation time to region 916 of views 912 and 914. Region 908 of views 902 and 904 corresponds to region 918 of views 912 and 914. Additionally, the standard deviations of activations time for both models are both derived from the same torso-surface potentials for one subject, were similar (17.6 and 15.5 ms). The overall pattern of cardiac activation and measures of dispersion of cardiac activation times are thus not dependent on a specific heart-torso model. Using a generic heart-torso model may allow a user to create an isochrone model of the cardiac activation time suitable for diagnosis and observation while avoiding expense, inconvenience, and radiation exposure that may be caused by the CT scan or other imaging that may be used to produce a patient-specific model of the heart of the patient.

Figure 10:
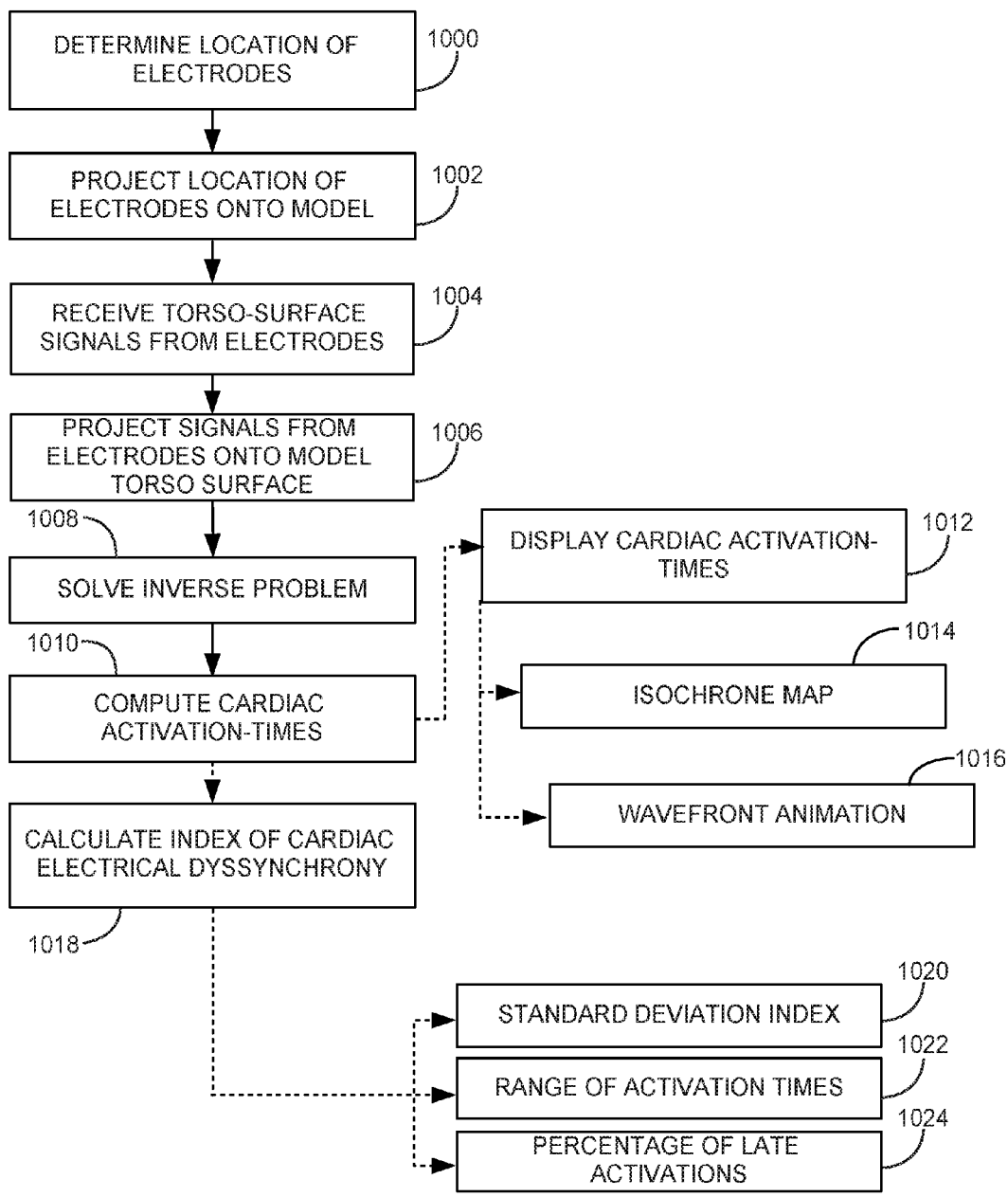
FIG. 10 is a flow diagram illustrating an example operation of a system to measure the cardiac electrical dyssynchrony of a patient via the cardiac activation times.

FIG. 10 is a flow diagram illustrating an example operation of a system to measure the cardiac electrical dyssynchrony of a patient via the cardiac activation times. Processing unit 500 determines the location of the electrodes 404, e.g., based on an analysis of imaging data by an electrode location registration module 524. Processing unit projects the locations of the electrodes onto a model torso, e.g., a selected model torso (1002).

A cardiac event, e.g., depolarization, occurs causing an electrical signal to propagate through the torso of the patient, and register on the electrodes distributed on the surface of the torso of the patient. The torso-surface potential signals sensed by the electrodes may be received by processing unit 500 (1004). The processing unit may project the signals onto the surface of the model torso based on the determined locations of the electrodes (1006).

The processing unit may solve the inverse problem of determining epicardial potentials based on torso-surface potentials (1008). The processing unit may then calculate cardiac activation times at a variety of locations of the model heart based upon the projected torso-surface potentials (1010). The cardiac activation times may be computed by, for example, determining the greatest negative slope of the epicardial electrogram potentials (1016) or by least squares minimization in the solution of the inverse problem (1018). The cardiac activation time may be displayed (1012). Examples of potential methods for displaying cardiac activation times include isochrone maps (1014) and a movie depicting the progression of the wavefront over the model heart (1016). The processing unit may be configured to allow a user select between, or display simultaneously, various display modes, including the wave front movie and isochrone maps. Additionally, one or more indices of cardiac electrical dyssynchrony may be calculated (1018), including the SDAT (1020), RAT (1022), and PLAT (1024).

For solving the inverse problem (1008), epicardial potentials may be computed from projected torso-surface potentials assuming a source-less volume conductor between the heart and the torso in an inverse Cauchy problem for Laplace's equation. Alternatively, an analytic relation between torso-surface potentials and the cardiac transmembrane potential may be assumed. Additionally, cardiac activation times may be estimated (1010) from the steepest negative slope of the epicardial electrograms determined from the inverse solution of the torso-surface potential/ epicardial potential transformation. In other examples, model torso-surface potentials may be simulated based on the analytic relationship approach to determining the cardiac transmembrane potential from torso-surface potential. Cardiac activation times (parameters in the analytic relationship) may be computed based on minimizing the least square difference between the projected model torso-surface potentials and simulated torso-surface potentials.

In some examples, the construction of a torso-surface activation times isochrone map (1014), wavefront animation (1016), or other graphical representation of cardiac electrical dyssynchrony, as well as the calculation of indices of cardiac electrical dyssynchrony (1018), may be performed for a particular region of the model heart based the computed cardiac activation times in such regions. Graphical representations and indices of cardiac electrical dyssynchrony may be determined for each of a plurality of regions based on the computed cardiac activation times in such regions. In some examples, the representations and indices for various regions may be presented together or compared.

Figure 11:
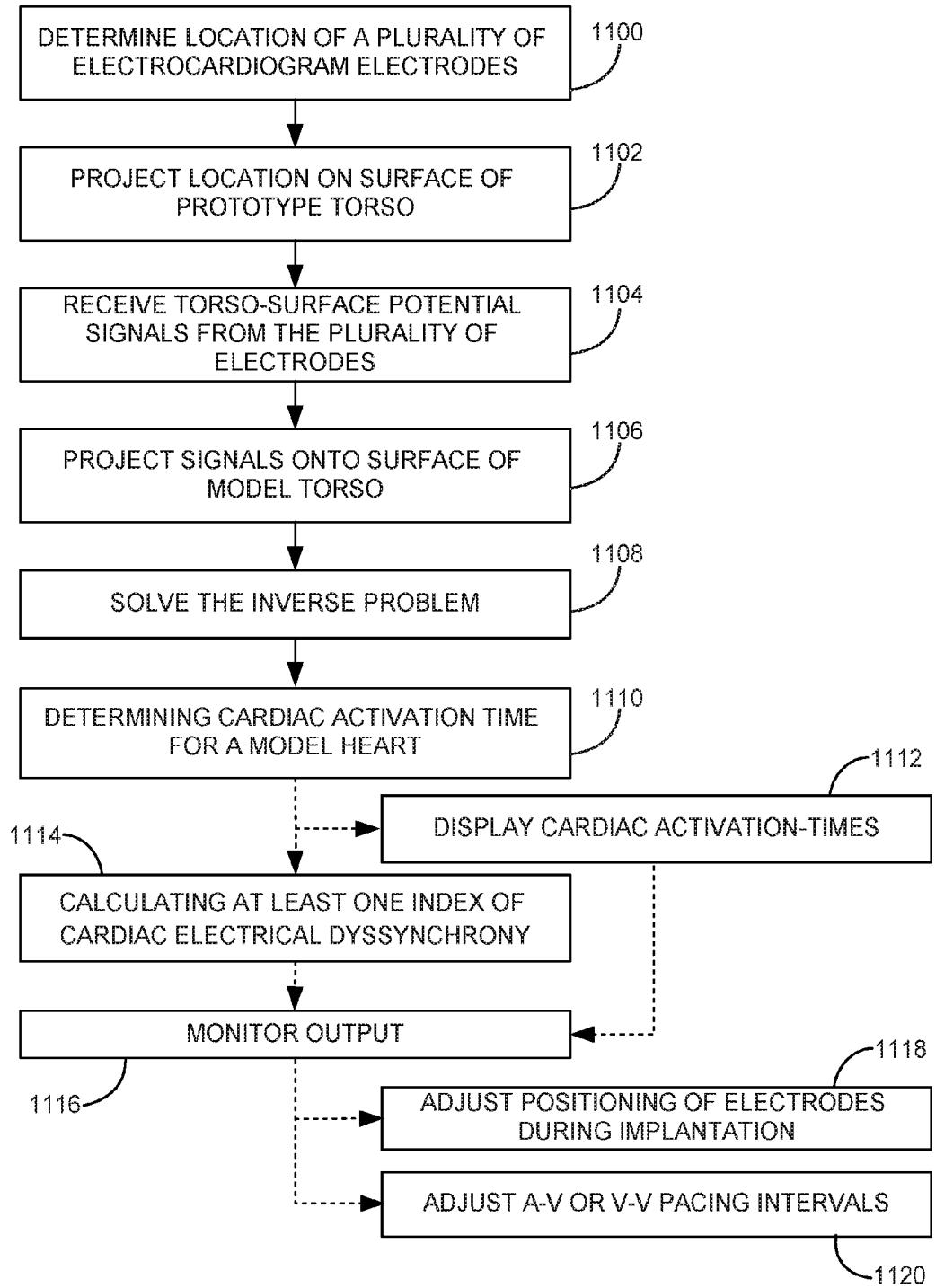
FIG. 11 is a flow diagram illustrating an example technique for configuring CRT based on an assessment of cardiac electrical dyssynchrony of a patient via the cardiac activation times.

FIG. 11 is a flow diagram illustrating an example technique for measuring the cardiac electrical dyssynchrony of a patient via determined cardiac activation times. The techniques may comprise determining the location of a plurality of electrodes (1100), projecting the location of the electrodes onto the surface of a model torso (1102), recording the output of the plurality of electrodes (1104), projecting the output of the plurality of the electrodes on the surface of the model torso (1106), solving the inverse problem (1108) and determining the cardiac activation times for a model heart from the projected torso-surface potentials (1110). The cardiac activation times may be displayed (1112). One or more indices of electrical dyssynchrony may be calculated (1114). The output, the indices of cardiac electrical dyssynchrony and cardiac activation time maps, may be monitored, allowing a user to diagnose the patient, adjust the position of CRT electrodes during implantation (1118), or adjust A-V or V-V pacing intervals of the CRT device (1120).

A user may monitor the output of the calculations (1116), e.g., the at least one indices of cardiac electrical dyssynchrony or the display of cardiac activation times. Monitoring these values may allow the user to diagnose a condition that might benefit from CRT or to evaluate the effectiveness of CRT. For example, the at least one index of cardiac electrical dyssynchrony may indicate the presence of damage to electrical conductivity of the heart of the patient, for example the presence of a left or right bundle branch block, that may not be apparent from the examination of a standard 12 lead ECG readout. A large SDAT indicates that the activation of the ventricles is occurring over a large time span, indicating that the depolarization of the ventricles is not occurring simultaneously. A large RAT also indicates a broad range of activation times and asynchronous contraction of the ventricles. A high PLAT may indicate that a specific region of the heart, e.g., the posterior regions more associated with the left ventricle, is failing to activate in concert with the measured QRS complex.

The user may adjust the positioning of CRT electrodes, e.g., electrodes 108, 110, and 112 of IMD 100 (FIG. 1) according to the displayed cardiac activation times or the indices of cardiac electrical dyssynchrony. For example, the processing unit, via a display, may implement system that displays shifting colors based on the percentage change of the indices of cardiac electrical dyssynchrony. As the position of the CRT electrodes are adjusted (1118), the displayed colors may shift from red to yellow to green based on the percentage improvement of the indices of cardiac electrical dyssynchrony. This may allow a user to rapidly determine if the adjustments of the CRT electrodes are having a positive effect on the symptoms of the patient. In another example, the user may adjust the A-V or V-V pacing intervals of an implanted CRT device (118). The minimum value of the indices of cardiac electrical dyssynchrony may indicate adequate pacing intervals. Isochrone maps or wave front propagation movies may also be used to aid in CRT adjustments or to diagnose conditions that may be responsive to CRT treatment.

As indicated above, to facilitate evaluating whether a patient is a candidate for CRT based on the monitored output (1116), the one or more indications of cardiac electrical dyssynchrony, e.g., indices or graphical indications, may be determined based on torso-surface activation times during both intrinsic conduction of the heart, and during CRT. Differences between the indications during intrinsic conduction and CRT may indicate that CRT would provide benefit for the patient, e.g., that the patient is a candidate for CRT. Furthermore, during implantation or a follow-up visit, the one or more indications of cardiac electrical dyssynchrony may be determined for each of a plurality of lead positions, electrode configurations, or other parameter values based on torso-surface activation times resulting from delivery of CRT at the positions, or with the electrode configurations or parameter values. In this manner, differences between cardiac electrical dyssynchrony indications associated with various locations, electrode configurations, or parameter values may be compared to determine preferred locations, configurations, or values.

In one or more embodiments, indices or metrics of electrical dyssynchrony and electrical activation patterns are determined from surface ECG electrodes associated with sensing device 400a, 400b. Vector optimization can also be achieved through implementing features described herein.

Figure 12:
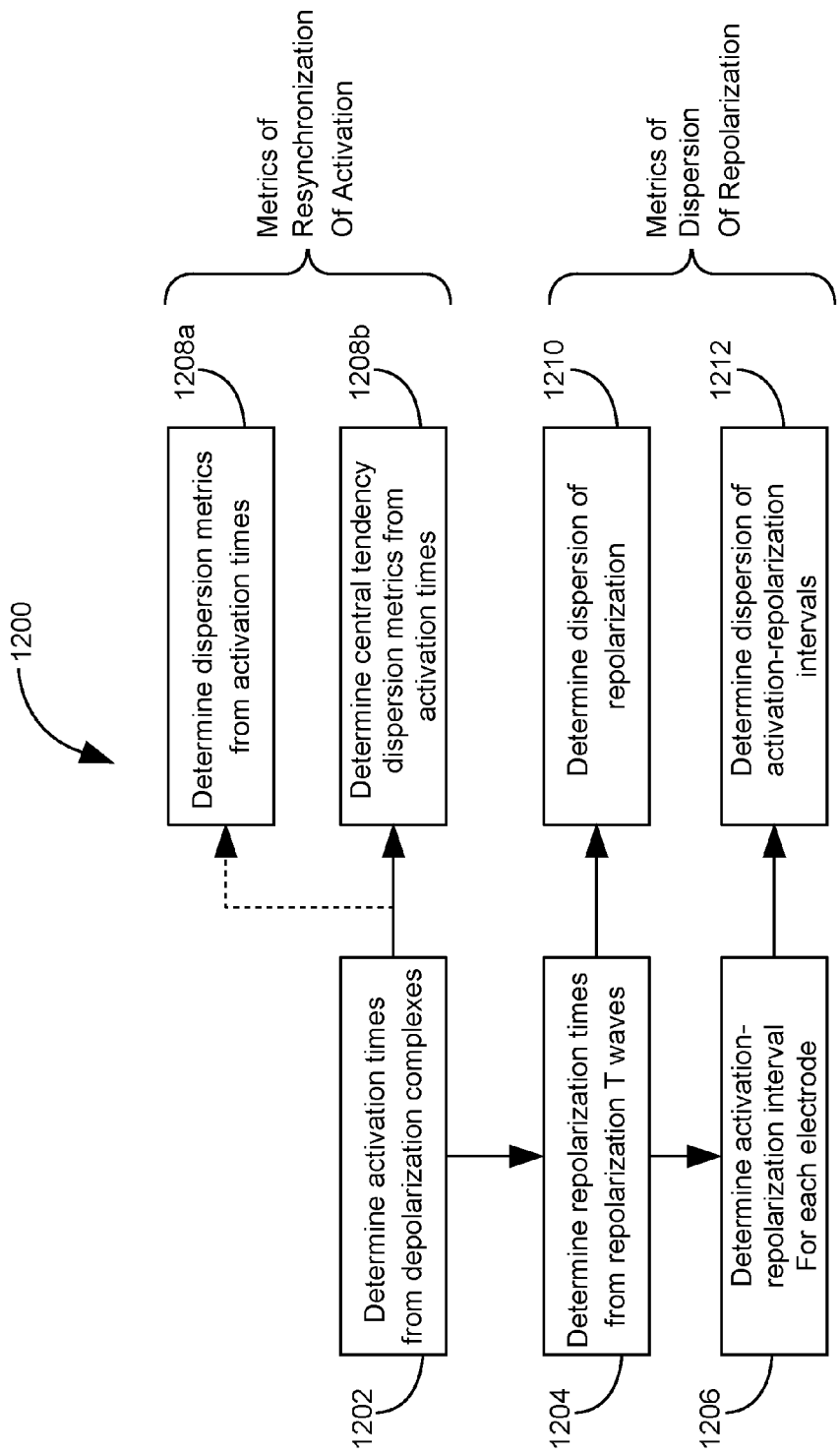
FIG. 12 is a flow diagram illustrating an example operation of a system to determine an optimal location of a lead through processing resynchronization of activation data and/or dispersion of repolarization data.

FIG. 12 is a flow diagram illustrating an exemplary method 1200 in which a sensing device 404a, 404b is employed to determine, prior to implant, functional electrical metric data used to determine efficacy of cardiac resynchronization for an implant of an IMD 100. Method 1200 can also be used to determine the effectiveness of CRT for a patient.

As used herein, metric is defined as a standard of measurement. Functional electrical metrics comprise resynchronization of activation metrics and/or dispersion of repolarization metrics. Exemplary cardiac resynchronization of activation metrics include dispersion metrics and central tendency metrics applied on activation-times obtained from electrical signals (e.g. QRS complex on surface ECG) indicative of cardiac depolarization. Dispersion metrics include standard deviation, range, and interquartile deviation of activation times measured with a plurality of electrodes. In comparison, central tendency is a mean, a median, or a mode, for example, of the absolute values of the activation times associated with signals acquired from electrodes. Central tendency is designated as Y in the figures.

Dispersion of ventricular repolarization, assessed as QT dispersion in the ECG or by multiple monophasic action potential (MAP) recordings, is defined as the difference between the earliest and latest repolarization. Exemplary dispersion of cardiac repolarization metrics include standard deviation, range, and interquartile difference of the recovery times and/or activation-recovery intervals associated with electrical signals (e.g. T-waves on surface ECG) indicative of cardiac repolarization.

At block 1202, one or more activation times are determined from depolarization complexes sensed from electrodes on sensing device 400a,b. Depolarization of the ventricles occurs before contraction of the ventricles. A depolarization wave spreads through the ventricles and is exhibited by the QRS complex.

One or more resynchronization of activation metrics can be determined at one or more blocks 1208a,b. At block 1208a, metrics of dispersion (e.g. one or more of measures like standard deviation, range, interquartile difference etc.) are computed from activation times of all or a subset (e.g. left-sided electrodes only) of electrodes.

Yet another metric of resynchronization of activation can be determined at block 1208b. At block 1208b, metrics of central tendency (e.g. mean, median, mode) of activation times corresponding to all or a subset (e.g. left-sided electrodes only) of electrodes are determined. As indicated by the ghost (dotted) lines in FIG. 12, processor 502 can execute computer instructions in blocks 1208a,b at the same time or about the same time.

In one or more embodiments, metrics of dispersion of repolarization are determined at block 1204. Ventricular repolarization is exemplified by T waves on a surface ECG or a cardiac electrogram (e.g. Twave peak, Twave end, Twave dV/dt max) that are acquired from electrodes on sensing device 400a, 400b.

At block 1210, dispersion of repolarization metrics (e.g. standard deviation, range, interquartile difference etc.) are computed for signals acquired from all or a subset (e.g. left-sided electrodes only) of electrodes.

At block 1206, an activation-repolarization interval (ARI) corresponding to each electrode on sensing device 404a,b is determined by calculating the difference between the repolarization time and the corresponding activation time. The ARI is the interval between a point selected on the QRS wave to represent the activation time and a point selected on the T-wave to represent the recovery time on an ECG or cardiac electrogram (EGM) signal.

At block 1212, computation of dispersion metrics (e.g. standard deviation, range, interquartile difference etc.) is performed on ARI from all or a subset (e.g. left-sided electrodes only) of electrodes. The functional electrical metrics, determined from executing the computer instructions of method 1200, are then stored into memory.

Figure 13:
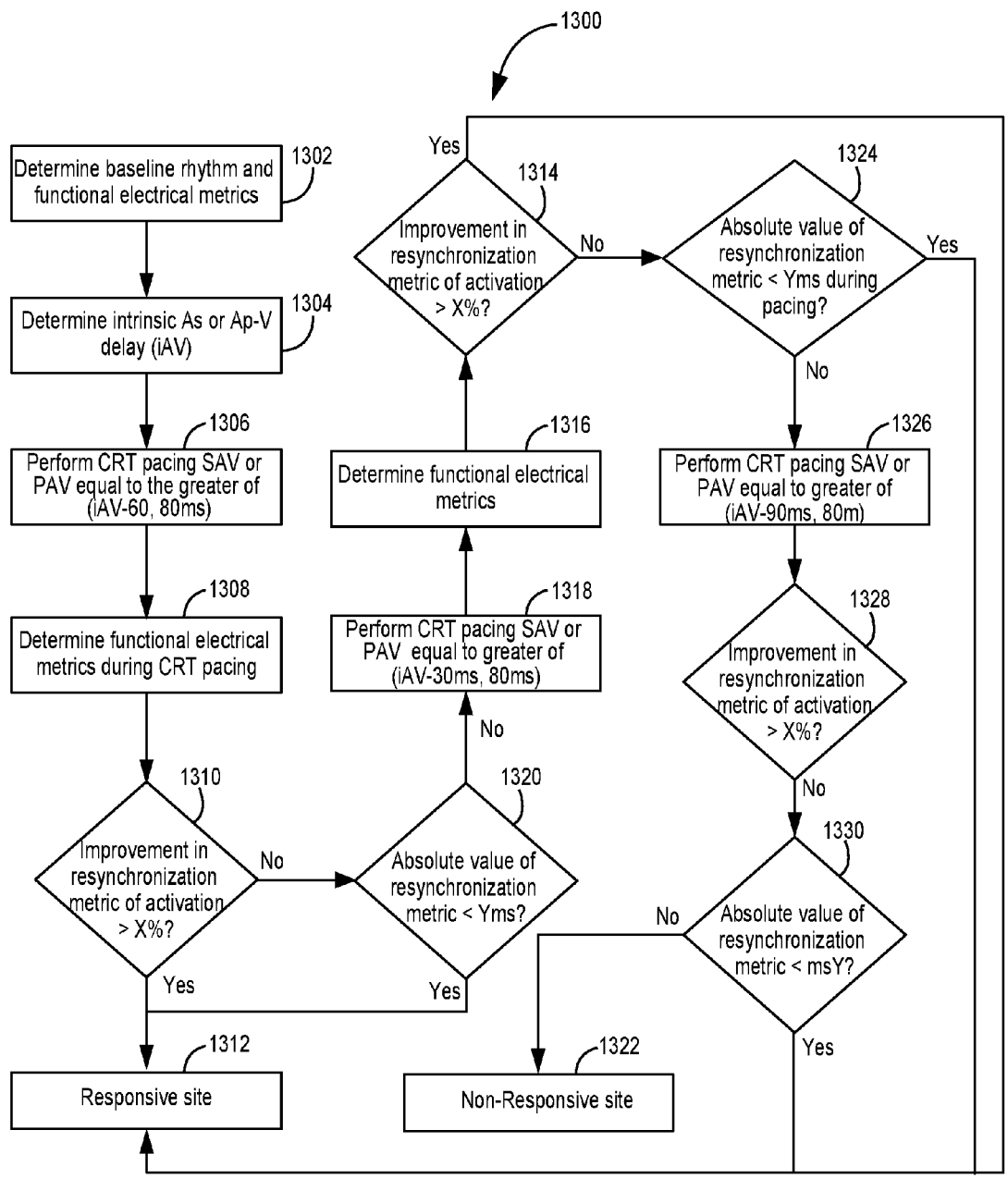
FIG. 13 is a flow diagram illustrating an example operation of a system that requires a single functional electrical metric requirement to be substantially satisfied in order to determine whether a site is responsive for stable non-tachycardia baseline with at least some 1:1 atrioventricular (AV) rhythm.

FIG. 13 is a flow diagram illustrating an exemplary method 1300 in which a system is employed to determine whether a patient, exhibiting a stable non-tachycardia baseline with at least some 1:1 atrial to ventricular (AV) conduction, is responsive to CRT pacing. Non-tachycardia is a heart rate or pattern that is not tachycardia (i.e. 100+ beats per minute (bpm) in a resting adult). Supraventricular tachycardia (SVT) is an example of an elevated heart rate but the baseline pattern is typically not as serious as tachycardia. Stable non-tachycardia baseline patients can possess characteristics of a cardiac condition (e.g. tiredness, cannot walk a normal distance without resting, nausea, and an elevated heart rate). Excluding a normal heart rate level, exemplary elevated heart rates can range from 120 bpm or less, 100 bpm or less, or 90 bpm or less. Identifying responsive sites in non-arrhythmic rhythm patients at the time of implant can potentially lead to better patient outcomes and reduce the burden of healthcare costs in future patient management.

Method 1300 begins at block 1302 in which a baseline rhythm and one or more functional electrical metrics are determined. Baseline rhythm (also simply referred to as a baseline) is the rhythm of the patient before receiving resynchronization therapy. For example, the baseline rhythm may include one of sinus rhythm, atrial pacing, right ventricular only pacing with or without synchronization to atria. The baseline electrical functional metrics are determined by measuring electrical activation times and repolarization times without resynchronization pacing.

At block 1304, a baseline atrioventricular (iAV) delay is determined. A patient's baseline AV conduction time is the time between a baseline atrial (e.g., right atrium) event (e.g., atrial pace or intrinsic atrial event (depolarization)) and a baseline ventricular (e.g., right ventricle) event (depolarization). Depolarization of the atria is sensed by an IMD when the heart naturally depolarizes. For example, the baseline events may be the intrinsic atrio-ventricular rhythm. As used herein, an "intrinsic" ventricular event or conduction is one that occurs or is conducted naturally. An exemplary method for sampling iAV is described relative to application Ser. No. 13/193,735 entitled "MODIFICATION OF AV CONDUCTION TIME SAMPLING RATE," filed on Jul. 29, 2011, incorporated by reference in its entirety. iAV is calculated by acquiring the intrinsic atrial sense (As) or atrial pace (Ap) and subtracting a ventricular (V) beat therefrom. At block 1306, CRT pacing is performed using pacemaker timed intervals. Pacemaker timed intervals end with ventricular pacing pulses and start with either a sensed atrial event or a paced atrial event. In particular, CRT pacing is performed using a sensed AV (SAV) interval (i.e. an interval starting with a sensed atrial event and ending with ventricular pacing pulses) or a paced AV (PAV) interval (i.e. an interval starting with a paced atrial event and ending with ventricular pacing pulses). The SAV or PAV is equal to the greater of iAV−60 ms and 80 ms. Specifically, the optimal AV ("AVopt" or "first AV delay") delay is set to whichever AV delay (i.e. SAV or PAV) is equal to the greater of iAV−60 ms or 80 ms.

At block 1308, one or more functional electrical metrics is determined using the SAV or PAV from operation 1306. At block 1310, a determination is made as to whether improvement of greater than X % is achieved in a resynchronization metric of activation. X % can be a value between 5% and 20%. Yet another range for X % may be a value between 10% and 25%. Yet another range for X % can be a value between 15% and 30%. Still yet another range can be between 10% and 100%.

The YES path from block 1310 indicates that improvement of greater than X % is achieved in a resynchronization metric of activation. The YES path from block 1310 continues to block 1312 in which the tissue site is determined to be a responsive site. A responsive site indicates the patient may benefit from CRT by placing an electrode at the tissue site and utilizing the functional electrical metrics indicated by method 1300. The NO path from block 1310 continues to block 1320.

At block 1320, a determination is made as to whether an absolute value of a resynchronization metric <Yms is attained. Y represents central tendency of the activation times. Y can be any value between 15 ms to about 150 ms. Yet another range for Y can be between 20 ms and 50 ms. Still yet another range for Y can be between 25 ms and 60 ms. If the absolute value of the resynchronization metric <Yms is attained, then the YES path from block 1320 continues to block 1312 in which it is determined that the tissue site is a responsive site. The NO path from block 1320 continues to block 1318 in which CRT pacing is performed at an AV delay (e.g. SAV or PAV) that is selected based upon whichever AV delay (e.g. SAV or PAV) is the greater of iAV−30 ms or 80 ms. The AV delay for block 1318, referred to as a second AV delay, is equivalent to AVopt+30 ms. By using two or more AV delays in method 1300, a patient's response or non-response to CRT can be confirmed.

At block 1316, one or more functional electrical metrics are determined while employing the SAV or PAV selected at block 1318. Preferably, functional electrical metrics that are determined at block 1316 include standard deviation and mean of global and/or regional electrical activation times; however, any previously listed functional electrical metrics can be determined at block 1316 for use in method 1300. At block 1314, while an IMD uses the SAV or PAV selected at block 1318, a determination is made as to whether an improvement of greater than X % is achieved in the resynchronization metric of activation. If an improvement of greater than X % is achieved in the resynchronization metric of activation, then the YES path from block 1314 continues to block 1312 in which the tissue site is determined to be responsive. The patient may benefit from CRT by placing an electrode at the tissue site deemed responsive to CRT while utilizing the functional electrical metrics indicated by method 1300.

The NO path from block 1314 continues to block 1324 in which a determination is made as to whether an absolute value of resynchronization metric <Yms during CRT pacing. If the absolute value of resynchronization metric <Yms during CRT pacing, then the YES path from block 1324 continues to block 1312 in which the tissue site is determined to be responsive. The patient may benefit from CRT by placing an electrode at the tissue site and utilizing the functional electrical metrics indicated by method 1300. The NO path from block 1324 continues to block 1326 in which CRT pacing is performed using an AV delay (i.e., SAV or PAV) that achieves the greater of iAV−90 ms or 80 ms.

At block 1328, a determination is made as to whether X % improvement is attained in a resynchronization metric of activation using the SAV or PAV from block 1326. The YES path from block 1328 continues to block 1312 determines that the tissue site is responsive and is a good site. The NO path from block 1328 continues to block 1330 in which a determination is made as to whether an absolute value of resynchronization metric <Yms. The YES path from block 1330 continues to block 1312 in which the tissue site is deemed responsive. The NO path from block 1330 continues to block 1322 in which the site is deemed non-responsive; therefore, an electrode should not be placed in this location.

Exemplary data was generated utilizing method 1300. The generated data includes baseline resynchronization metrics determined at block 1302. Two functional electrical metrics, metric 1 and metric 2, were employed. The first metric (i.e. metric 1) corresponds to standard deviation of activation times from all surface electrodes. The second metric corresponds to the standard deviation of activation times of electrodes which are on the left side of the torso. The baseline metrics, determined during intrinsic conduction, indicated an iAV of 160 ms, metric 1 is 55 ms, and metric 2 is 80 ms. In this example, a responsive site was determined to be a relative improvement in metric 1 of greater than 10% and/or metric 2 is less than 20 ms for placement of an electrode on a medical electrical lead.

Tables 1 and 2, presented below, summarize data generated for the resynchronization metrics during CRT pacing from site 1 and site 2, respectively.

TABLE 1

Resynchronization metrics during CRT Pacing from Site 1

|  | First AV | Second AV | Third AV |
| --- | --- | --- | --- |
| AV delay | iAV−60 ms | iAV−30 ms | 80 ms |
| Metric 1 | 58 ms | 59 ms | 52 ms |
| Metric 2 | 84 ms | 91 ms | 96 ms |
| Relative reduction in metric 1 | −5.40% | −6.77% | 3.63% |

From Table 1, a negative relative reduction occurred with iAV−60 ms and iAV−30 ms. Negative relative reduction involves an increased metric value during pacing compared to baseline. The more positive the relative reduction, the greater the improvement in resynchronization compared to the baseline. Substantially positive relative reduction involves resynchronization that is substantially improved compared to baseline. As indicated, the third AV delay is 80 ms because, in this example, iAV−90 ms—160 ms−90 ms=70 ms. Since 80 ms is greater of iAV−90 ms and 80 ms, a AV delay of 80 ms is set for the third AV delay. Based upon this data, Site 1 is non-responsive.

Site 2 is determined to be responsive; therefore, it is unnecessary to employ iAV−30 ms and iAV−90 ms. As shown in the table, the AV delay is set at iAV−60 ms. Metric 1 is 38 ms while metric 2 is 24 ms. The positive relative reduction shows a substantially improved resynchronization over the baseline.

TABLE 2

Resynchronization metrics during CRT Pacing from Site 2

|  | AV |
| --- | --- |
| AV delay | iAV−60 ms |
| Metric 1 | 38 ms |
| Metric 2 | 24 ms |
| Relative reduction in metric 1 | 34.00% |

Figure 14:
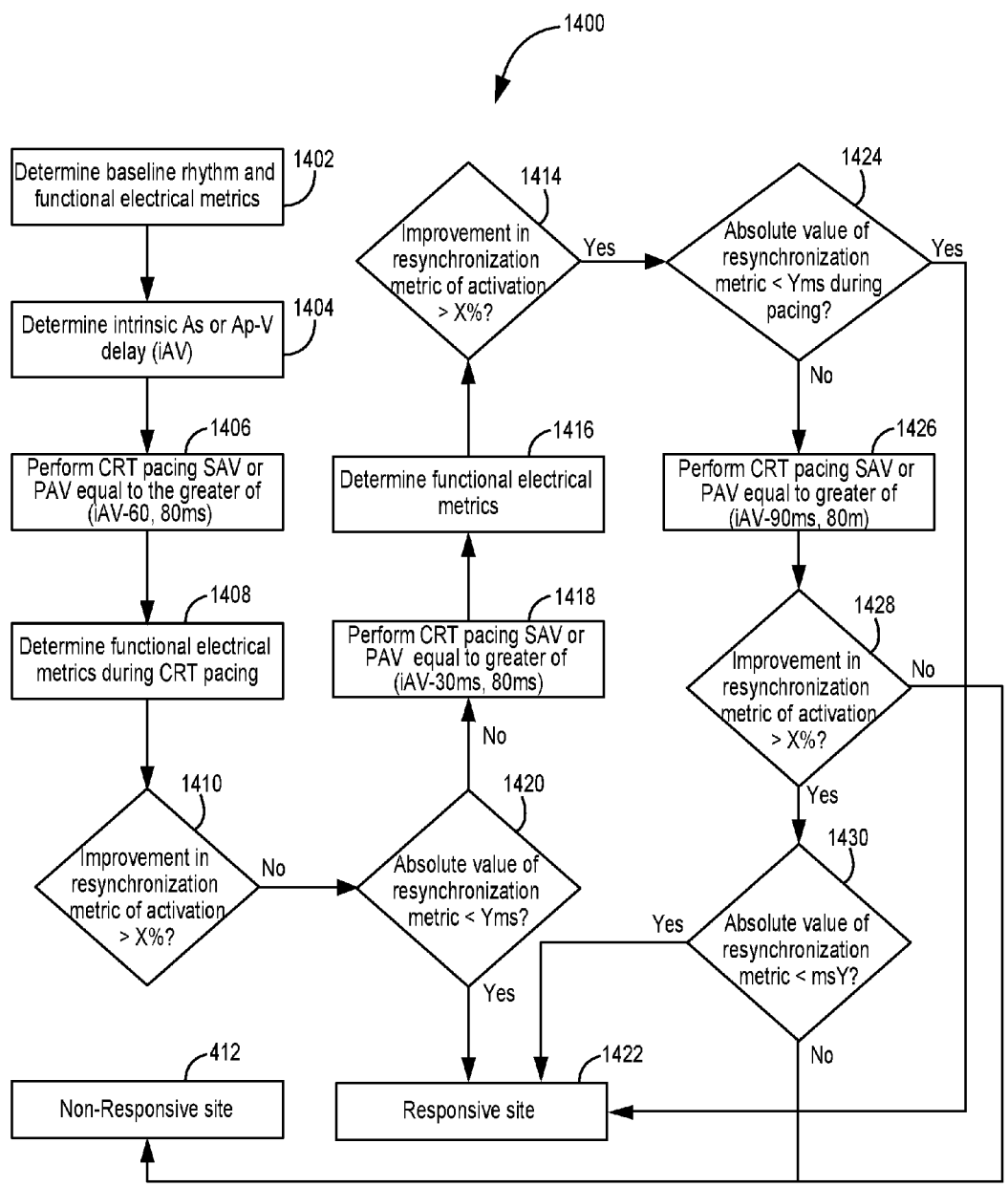
FIG. 14 is a flow diagram illustrating another embodiment of an exemplary operation of a system that requires two functional electrical metric requirements to be substantially satisfied in order to determine whether a site is responsive for stable non-tachycardia baseline with at least some 1:1 AV rhythm.

Method 1400 of flow diagram of FIG. 14 exemplifies a method which two functional electrical metric requirements are substantially met or must be met in order to select an optimal electrode on a lead. Method 1400 is the same or similar as the flow diagram of FIG. 13 as to blocks 1302, 1304, 1306, 1308, 1316, 1318, 1320, 1322, 1324, 1326 and 1330. In particular blocks 1302, 1304, 1306, 1308, 1316, 1318, 1320, 1322, 1324, 1326 and 1330 correspond to blocks 1402, 1404, 1406, 1408, 1416, 1418, 1420, 1422, 1424, 1426 and 1430, respectively; therefore the description of the 1300 blocks are incorporated herein. Additionally, variables such as X % and Y used in FIG. 14 possess the same or about the same ranges as previously described relative to FIG. 13.

Method 1400 is different from method 1300 based upon the paths exiting blocks 1410, 1414, and 1428. For example, at block 1410, a determination is made as to whether employing the functional electrical metrics at block 1408 improves the resynchronization metric of activation by X %. If so, the YES path from block 1410 continues to block 1420. In contrast, if the functional electrical metrics do not achieve X %, then the NO path from block 1410 continues to block 1418.

Paths exiting block 1414 is another difference to method 1300. At block 1414, a determination is made as to whether employing the functional electrical metrics at block 1408 improves the resynchronization metric of activation by X %. An affirmative response to block 1414 leads to block 1424 while a negative response leads to block 1426.

Paths exiting block 1428 is also different from method 1300. At block 1428, a determination is made as to whether employing the functional electrical metrics at block 1408 improves the resynchronization metric of activation by X %. An affirmative response to block 1428 leads to block 1430 while a negative response leads to block 1412.

Exemplary data was generated relative to four left ventricular (LV) electrodes (e.g. LV1, LV2, LV3, LV4) located on the left ventricular lead. Exemplary left ventricular leads that employ LV1-LV4 are shown and described in application Ser. No. 13/464,228, and Ser. No. 13/772,890, incorporated herein). The relative improvement of resynchronization is presented in Table 3 for each electrode and each metric. Electrodes able to elicit a positive response generally are able to achieve greater than 10% relative improvement in metric 1 and less than or equal to 20 ms for the metric 2 of resynchronization. According to the present example, LV1 and LV4 satisfy this criteria.

TABLE 3

Summary of LV electrode and resynchronization

| LV electrode | Metric 1--Relative improvement of resynchronization | Metric 2-- resynchronization |
| --- | --- | --- |
| LV1 | 12% | 12 ms |
| LV2 | −5% | 10 ms |
| LV3 | −6% | 15 ms |
| LV4 | 14% | 12 ms |

Data can also be generated as to dispersion of repolarization metrics. In this example, dispersion of repolarization metrics is used to break the tie between LV1 and LV4 with respect to determining optimal location from which to deliver pacing pulses. For example, dispersion of repolarization metric for LV1 equaled 60 ms while that for LV4 equaled 300 ms. Based upon this data, LV1 is the optimal electrode from which to pace.

In one or more embodiments, the cardiac improvement information may include dyssynchrony information. Dyssynchrony information may be defined as information indicative of the mechanical and/or electrical dyssynchrony of the heart. In at least one embodiment, the dyssynchrony information may include a standard deviation of ventricular activation times corresponding to electrodes on the surface array. Further, regional dyssynchrony may be also computed from the standard deviation of activation times corresponding to electrodes located in certain anatomic areas of the torso, for e.g. electrodes on the left side of the torso would be used to compute regional LV dyssynchrony.

Various examples of this disclosure have been described in which to select an optimal electrode from which to pace through the combination of relative changes in metrics of electrical dyssynchrony/activation from baseline to CRT pacing and/or absolute values of those metrics during CRT pacing may be used for discerning response to cardiac resynchronization therapy during pacing. For example, a X % reduction in electrical dyssynchrony or left ventricular electrical dyssynchrony <Y ms may be used to identify a good or optimal lead location. X % may be any value from 5% to 100% and Y may be any value from 15 to 150 ms. A site is designated as a bad location or non-responder location if the site does not yield the changes in electrical dyssynchrony metrics as described above during biventricular pacing at a plurality of A-V delays. For example, pacing may be performed at AV delays based on measurement of the intrinsic sensed or paced A-V timing (iSAV or iPAV). In one embodiment, pacing is performed at a sensed or paced A-V delay equal to iSAV–60 or iPAV–60 ms respectively. If desired changes in electrical activation and dyssynchrony parameters (as defined for a responsive site) are not obtained, pacing may be performed at a AV delay equal to the lesser of iSAV (or iPAV)–90 ms to about 80 ms. If desired changes are still not obtained, biventricular pacing may be performed at one additional A-V delay, iSAV (or iPAV)–30 ms. If electrical activation and electrical dyssynchrony metrics do not change favorably during pacing for any of these A-V delays. The site may be defined as a non-responder site and the lead may be moved to additional sites for automatic evaluation.

However, one of ordinary skill in the art will appreciate that various modifications may be made to the described embodiments without departing from the scope of the claims. For example, although SDAT, RAT and PLAT have been discussed as example statistical indices of the dispersion of activation times, other indices or metrics of the dispersion of the timing of depolarization may be determined according the techniques of this disclosure. As one example, a range of activation times between two specific regions, e.g., anterior and posterior, may be determined. As another example, a range or variability of activation times after excluding certain locations or regions may be determined according to the techniques of this disclosure. The excluded locations or regions may be those that are believed to be scar tissue, e.g., identified by low amplitude electrical signals, or locations or regions that are beyond the extent of the far-field QRS complex. In general, calculation of an index may include determining any statistical or other value based on the torso-surface or cardiac activation times, or some subset thereof. These and other examples are within the scope of the following claims.

The invention claimed is:

1. A method of cardiac pacing comprising:
a) sensing heart activity using a plurality of body-surface electrodes;
b) using a processor to determine
(i) a baseline rhythm from the sensed heart activity; and
(ii) a set of baseline functional electrical metrics based upon the baseline rhythm;
(c) delivering resynchronization pacing using a right ventricular electrode and pacing a left ventricular electrode or only pacing with a left ventricular electrode;
(d) using the processor to determine a set of functional electrical metrics relating to cardiac depolarization and repolarization in response to the resynchronization pacing;
(e) using the processor to determine whether relative reduction of at least one functional electrical metric from the set of functional electrical metrics in step d exceeds X % of its corresponding value from the set of baseline functional electrical metrics in step b;
(f) in response to determining that relative reduction of at least one functional electrical metric from the set of functional electrical metrics in step d exceeds X %, using the processor to determine whether an absolute value of at least one electrical metric from the set of the functional electrical metrics in step d is less than Y ms; and
(g) using the processor to determine that a site is responsive to cardiac resynchronization therapy (CRT) in response to determining whether step f) is met.

2. The method of claim 1 wherein the resynchronization pacing using a first SAV or first PAV equal to greater of (intrinsic AV–60 ms, 80 ms); and
using the processor to determine another set of functional electrical metrics relating to cardiac depolarization and repolarization in response to the resynchronization pacing.

3. The method of claim 2 further comprising:
using the processor to determine whether relative reduction of at least one functional electrical metric from the set of functional electrical metrics in the step of claim 2 exceeds X % of its corresponding value from the set of baseline functional electrical metrics.

4. The method of claim 3 wherein
the resynchronization pacing using a second SAV or a second PAV equal to greater of (intrinsic AV–30 ms, 80 ms); and
using the processor to determine another set of functional electrical metrics relating to cardiac depolarization and repolarization in response to the resynchronization pacing.

5. The method of claim 4 further comprising:
using the processor to determine whether relative reduction of at least one functional electrical metric from the set of functional electrical metrics in the step of claim 2 exceeds X % of its corresponding value from the set of baseline functional electrical metrics.

6. The method of claim 3 further comprising:
in response to determining relative reduction of at least one functional electrical metric from the set of functional electrical metrics in the step of claim 2 exceeds X %, using the processor to determine whether an absolute value of at least one electrical metric from the set of the functional electrical metrics is less than Y ms; and
in response to determining the absolute value of at least one electrical metric from the set of the functional electrical metrics is less than Y ms, using the processor to determine that a site is responsive to cardiac resynchronization therapy (CRT).

7. The method of claim 3 further comprising:
in response to determining relative reduction of at least one functional electrical metric from the set of functional electrical metrics in the step of claim 2 does not exceed X %, delivering resynchronization pacing using a right ventricular electrode and a pacing left ventricular electrode or only pacing with a left ventricular electrode, the resynchronization pacing using a SAV or PAV equal to greater of (intrinsic AV−90 ms, 80 ms).

8. The method of claim 3 further comprising:
in response to determining relative reduction of at least one functional electrical metric from the set of functional electrical metrics in the step of claim 2 does not exceed X %, delivering resynchronization pacing using a right ventricular electrode and a pacing left ventricular electrode or only pacing with a left ventricular electrode, the resynchronization pacing using a SAV or PAV equal to greater of (intrinsic AV−30 ms, 80 ms).

9. The method of claim 7 further comprising:
determining whether relative reduction of at least one functional electrical metric from the set of functional electrical metrics exceeds X % of its corresponding value from the set of baseline functional electrical metrics.

10. The method of claim 9, further comprising:
using the processor to determine that a site is responsive to cardiac resynchronization therapy (CRT) in response to determining whether a step in claim 7 is met.

11. The method of claim 9, further comprising:
using the processor to determine that a site is nonresponsive to cardiac resynchronization therapy (CRT) in response to determining whether a step in claim 7 is not met.

12. The method of claim 9, further comprising:
using the processor to determine whether an absolute value of at least one electrical metric from the set of the functional electrical metrics is less than Y ms; and
in response to determining the absolute value of at least one electrical metric from the set of the functional electrical metrics is less than Y ms, determining that a site is responsive to cardiac resynchronization therapy (CRT).

13. The method of claim 1 wherein functional electrical metrics are indicative of electrical dyssynchrony during a cardiac depolarization process and dispersion of repolarization during a cardiac repolarization process.

14. The method of claim 13 wherein the functional electrical metrics are associated with at least one resynchronization of activation metric.

15. The method of claim 14 wherein the resynchronization of activation metric relates to dispersion of electrical activation times corresponding to a plurality of surface electrodes on a torso or on certain predefined anatomic areas of the torso.

16. The method of claim 15 wherein at least one resynchronization of activation metric is standard deviation of activation times acquired from the plurality of body-surface electrodes.

17. The method of claim 15 wherein at least one resynchronization of activation metric is standard deviation of activation times of only left-sided electrodes of the plurality of body-surface electrodes.

18. The method of claim 14 wherein at least one resynchronization of activation metric is associated with central tendency of electrical activation times corresponding to the plurality of body-surface electrodes on a torso or on certain predefined anatomic areas of the torso.

19. The method of claim 18 wherein the central tendency of electrical activation times reflects one of an average global activation time and an average regional activation time.

20. The method of claim 1, wherein X % ranges from about 5% to about 100%.

21. The method of claim 1, wherein Y ranges from about 15 ms to about 150 ms.

22. The method of claim 1 wherein a measure of dispersion may include standard deviation, range or interquartile deviation of activation times, repolarization times, activation-recovery intervals associated with a plurality of surface electrodes.

23. The method of claim 1, wherein central tendency is one of a mean, a median, mode or a sum of absolute values of activation times associated with a plurality of surface electrodes.

24. A system of cardiac pacing comprising:
(a) sensing heart activity using a plurality of body-surface electrodes;
(b) using a processor means for determining:
a baseline rhythm sensed from the heart activity; and
a set of baseline functional electrical metrics from the baseline rhythm;
(c) delivering resynchronization pacing using a right ventricular electrode and a pacing left ventricular electrode or only with a left ventricular electrode;
(d) using the processor means for determining:
(i) a set of functional electrical metrics relating to cardiac depolarization and repolarization in response to resynchronization pacing;
(ii) whether relative reduction of at least one functional electrical metric from the set of functional electrical metrics in step d exceeds X % of its corresponding value from the set of baseline functional electrical metrics in step b;
(f) in response to determining that relative reduction of at least one functional electrical metric from the set of functional electrical metrics in step d exceeds X %, using the processor means for determining whether an absolute value of at least one electrical metric from the set of the functional electrical metrics in step d is less than Y ms; and
(g) the processor means for determining that a site is responsive to cardiac resynchronization therapy (CRT) in response to determining whether step f) is met.

25. The system of claim 24 further comprising:
delivering resynchronization pacing using a right ventricular electrode and a pacing left ventricular electrode or only with a left ventricular electrode, the resynchronization pacing using a first SAV or first PAV equal to greater of (intrinsic AV−60 ms, 80 ms); and
the processor means for determining another set of functional electrical metrics relating to cardiac depolarization and repolarization in response to resynchronization pacing.

26. The system of claim 25 further comprising:
the processor means for determining whether relative reduction of at least one functional electrical metric from the set of functional electrical metrics in the step of claim 24 exceeds X % of its corresponding value from the set of baseline functional electrical metrics.

27. The system of claim 26 further comprising:
delivering resynchronization pacing using a right ventricular electrode and a pacing left ventricular electrode or only with a left ventricular electrode, the resynchronization pacing using a second SAV or a second PAV equal to greater of (intrinsic AV−30 ms, 80 ms); and
the processor means for determining another set of functional electrical metrics relating to cardiac depolarization and repolarization in response to resynchronization pacing.

28. The system of claim 27 further comprising:
the processor means for determining whether relative reduction of at least one functional electrical metric from the set of functional electrical metrics in the step of claim 25 exceeds X % of its corresponding value from the set of baseline functional electrical metrics.

29. The system of claim 26 further comprising:
in response to determining relative reduction of at least one functional electrical metric from the set of functional electrical metrics in the step of claim 25 exceeds X %, the processor means for determining whether an absolute value of at least one electrical metric from the set of the functional electrical metrics is less than Y ms; and
in response to determining the absolute value of at least one electrical metric from the set of the functional electrical metrics is less than Y ms, the processor means for determining that a site is responsive to cardiac resynchronization therapy (CRT).

30. The system of claim 26 further comprising:
in response to determining relative reduction of at least one functional electrical metric from the set of functional electrical metrics in the step of claim 25 does not exceed X %, delivering resynchronization pacing using a right ventricular electrode and a pacing left ventricular electrode or only with a left ventricular electrode, the resynchronization pacing using a SAV or PAV equal to greater of (intrinsic AV−90 ms, 80 ms).

31. The system of claim 26 further comprising:
in response to determining relative reduction of at least one functional electrical metric from the set of functional electrical metrics in the step of claim 25 does not exceed X %, delivering resynchronization pacing using a right ventricular electrode and a pacing left ventricular electrode or only with a left ventricular electrode, the resynchronization pacing using a SAV or PAV equal to greater of (intrinsic AV−30 ms, 80 ms).

32. The system of claim 30 further comprising:
the processor means for determining whether relative reduction of at least one functional electrical metric from the set of functional electrical metrics exceeds X % of its corresponding value from the set of baseline functional electrical metrics.

33. The system of claim 32, further comprising:
the processor means for determining that a site is responsive to cardiac resynchronization therapy (CRT) in response to determining whether a step in claims 24 to 32 is met.

34. The system of claim 32, further comprising:
the processor means for determining that a site is nonresponsive to cardiac resynchronization therapy (CRT) in response to determining whether a step in claims 24 to 33 is not met.

35. The system of claim 32, further comprising:
the processor means for determining whether an absolute value of at least one electrical metric from the set of the functional electrical metrics is less than Y ms; and
in response to determining the absolute value of at least one electrical metric from the set of the functional electrical metrics is less than Y ms, determining that a site is responsive to cardiac resynchronization therapy (CRT).

36. The system of claim 24 wherein functional electrical metrics are indicative of electrical dyssynchrony during a cardiac depolarization process and dispersion of repolarization during a cardiac repolarization process.

37. The system of claim 36 wherein the functional electrical metrics are associated with at least one resynchronization of activation metric.

38. The system of claim 37 wherein the resynchronization of activation metric relates to dispersion of electrical activation times corresponding to the plurality of body-surface electrodes on a torso or on certain predefined anatomic areas of the torso.

39. The system of claim 38 wherein at least one resynchronization of activation metric is standard deviation of activation times acquired from all torso electrodes.

40. The system of claim 39 wherein at least one resynchronization of activation metric is standard deviation of activation times of only left-sided electrodes of the torso electrodes.

41. The system of claim 37 wherein at least one resynchronization of activation metric is associated with central tendency of electrical activation times corresponding to a plurality of body-surface electrodes on a torso or on certain predefined anatomic areas of the torso.

42. The system of claim 41 wherein the central tendency of electrical activation times reflects one of an average global activation time and an average regional activation time.

43. The system of claim 24, wherein X % ranges from about 5% to about 100%.

44. The system of claim 24, wherein Y ranges from about 15 ms to about 150 ms.

45. The system of claim 24 wherein a measure of dispersion may include standard deviation, range or interquartile deviation of activation times, repolarization times, activation-recovery intervals associated with a plurality of body-surface electrodes.

46. The system of claim 24, wherein central tendency is one of a mean, a median, mode or a sum of absolute values of activation times associated with a plurality of body-surface electrodes.

47. A non-transitory, computer-readable storage medium comprising instructions that, when executed, cause a processor included in a medical device system to:
a) acquiring heart activity from a plurality of body-surface electrodes;
(b) determining a baseline rhythm from the acquired heart activity and a set of baseline functional electrical metrics in response to determining the baseline rhythm;
(c) cause delivery of resynchronization pacing using a right ventricular electrode and a pacing left ventricular electrode or only with a left ventricular electrode;
(d) determining a set of functional electrical metrics relating to cardiac depolarization and repolarization in response to the resynchronization pacing;
(e) determining whether relative reduction of at least one functional electrical metric from the set of functional electrical metrics in step d exceeds X % of its corresponding value from the set of baseline functional electrical metrics in step b;
(f) in response to determining that relative reduction of at least one functional electrical metric from the set of functional electrical metrics in step d exceeds X %, determining whether an absolute value of at least one electrical metric from the set of the functional electrical metrics in step d is less than Y ms; and
(g) determine that a site is responsive to cardiac resynchronization therapy (CRT) in response to determining whether step f) is met.

* * * * *